(12) United States Patent
Zhang et al.

(10) Patent No.: US 12,390,185 B2
(45) Date of Patent: Aug. 19, 2025

(54) AUTOMATED BREAST ULTRASOUND EQUIPMENT AND METHODS USING ENHANCED NAVIGATOR AIDS

(71) Applicant: QVIEW MEDICAL INC., Los Altos, CA (US)

(72) Inventors: Wei Zhang, San Jose, CA (US); Shih-Ping Wang, Los Altos, CA (US); Alexander Schneider, Los Altos, CA (US); Harlan Romsdahl, Half Moon Bay, CA (US); Thomas Neff, Newark, CA (US)

(73) Assignee: QView Medical Inc., Los Altos, CA (US)

(*) Notice: Subject to any disclaimer, the term of this patent is extended or adjusted under 35 U.S.C. 154(b) by 537 days.

(21) Appl. No.: 17/942,749

(22) Filed: Sep. 12, 2022

(65) Prior Publication Data

US 2023/0018351 A1 Jan. 19, 2023

Related U.S. Application Data

(60) Division of application No. 16/667,526, filed on Oct. 29, 2019, now Pat. No. 11,439,362, which is a
(Continued)

(51) Int. Cl.
*A61B 8/08* (2006.01)
*A61B 8/00* (2006.01)
(Continued)

(52) U.S. Cl.
CPC .............. *A61B 8/0825* (2013.01); *A61B 8/14* (2013.01); *A61B 8/4209* (2013.01);
(Continued)

(58) Field of Classification Search
None
See application file for complete search history.

(56) References Cited

U.S. PATENT DOCUMENTS 6,876,879 B2 * 4/2005 Dines ..................... A61B 8/483
128/915
8,014,576 B2 * 9/2011 Collins ................ G06V 10/764
382/128

(Continued)

*Primary Examiner* — Samah A Beg
(74) *Attorney, Agent, or Firm* — Wissing Miller LLP

(57) ABSTRACT

A method and system acquiring, processing and displaying breast ultrasound images in a way that makes breast ultrasound screening more practical and thus more widely used, and reduces the occurrence of missing cancers in screening and diagnosis, using automated scanning of chestwardly compressed breasts with ultrasound. Enhanced, whole-breast navigator overview images are produced from scanning breasts with ultrasound that emphasize abnormalities in the breast while excluding obscuring influences of non-breast structures, particularly those external to the breast such as ribs and chest wall, and differentiating between likely malignant and likely benign abnormalities and otherwise enhancing the navigator overview image and other images, thereby reducing the time to read, screen, and/or diagnose to practical time limits and also reduce screening or diagnostic errors.

20 Claims, 29 Drawing Sheets

Related U.S. Application Data continuation of application No. 15/716,650, filed on Sep. 27, 2017, now Pat. No. 10,603,007, which is a continuation of application No. 14/555,408, filed on Nov. 26, 2014, which is a continuation-in-part of application No. PCT/US2014/067758, filed on Nov. 26, 2014, which is a continuation-in-part of application No. 14/448,607, filed on Jul. 31, 2014, now Pat. No. 9,439,321, which is a continuation-in-part of application No. PCT/US2014/048897, filed on Jul. 30, 2014, and a continuation-in-part of application No. 14/084,589, filed on Nov. 19, 2013, now abandoned, which is a continuation-in-part of application No. 14/044,842, filed on Oct. 2, 2013, now Pat. No. 9,826,958, which is a continuation-in-part of application No. 12/839,371, filed on Jul. 19, 2010, now abandoned.

(60) Provisional application No. 62/003,448, filed on May 27, 2014, provisional application No. 61/910,139, filed on Nov. 29, 2013, provisional application No. 61/860,900, filed on Jul. 31, 2013, provisional application No. 61/830,241, filed on Jun. 3, 2013, provisional application No. 61/728,166, filed on Nov. 19, 2012, provisional application No. 61/709,136, filed on Oct. 2, 2012.

(51) Int. Cl.
*A61B 8/14* (2006.01)
*G06T 7/00* (2017.01)

(52) U.S. Cl.
CPC .......... *A61B 8/4455* (2013.01); *A61B 8/4461* (2013.01); *A61B 8/4494* (2013.01); *A61B 8/463* (2013.01); *A61B 8/483* (2013.01); *A61B 8/5223* (2013.01); *G06T 7/0012* (2013.01); *A61B 8/145* (2013.01); *A61B 8/403* (2013.01); *A61B 8/4218* (2013.01); *A61B 8/4281* (2013.01); *A61B 8/4405* (2013.01); *A61B 8/469* (2013.01); *A61B 8/54* (2013.01)

(56) References Cited

U.S. PATENT DOCUMENTS

| | | | |
|---|---|---|---|
| 2005/0089205 A1* | 4/2005 | Kapur | A61B 8/483 382/128 |
| 2005/0171430 A1* | 8/2005 | Zhang | A61B 8/463 600/437 |
| 2015/0052471 A1* | 2/2015 | Chen | A61B 6/025 715/771 |

* cited by examiner

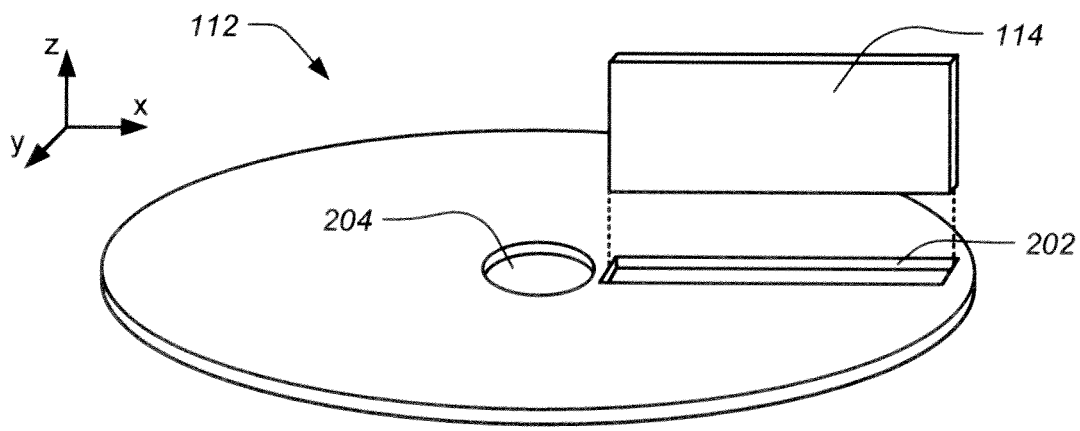
FIG. 2
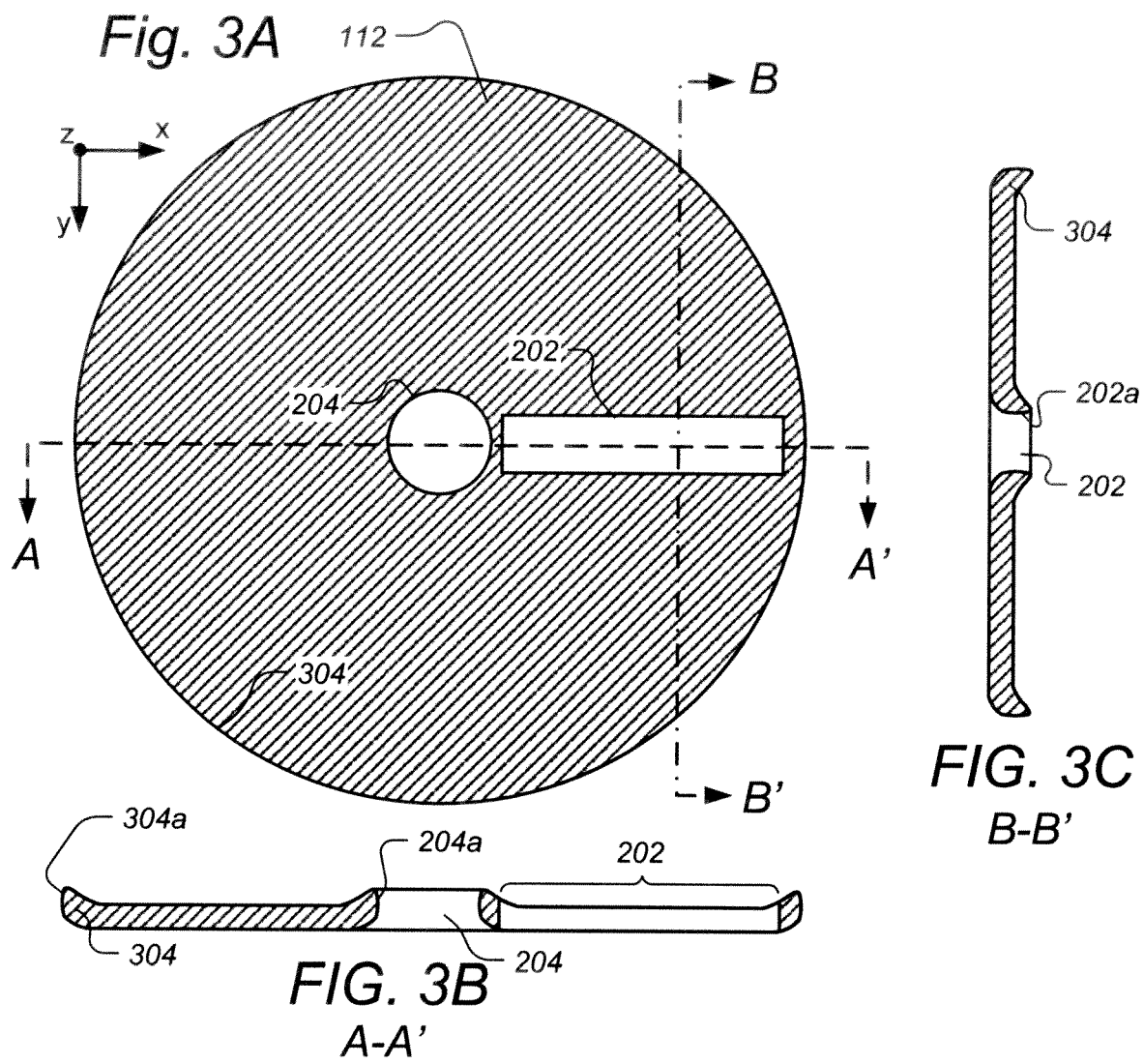
Fig. 3A
FIG. 3B
A-A'
FIG. 3C
B-B'

FIG. 12A
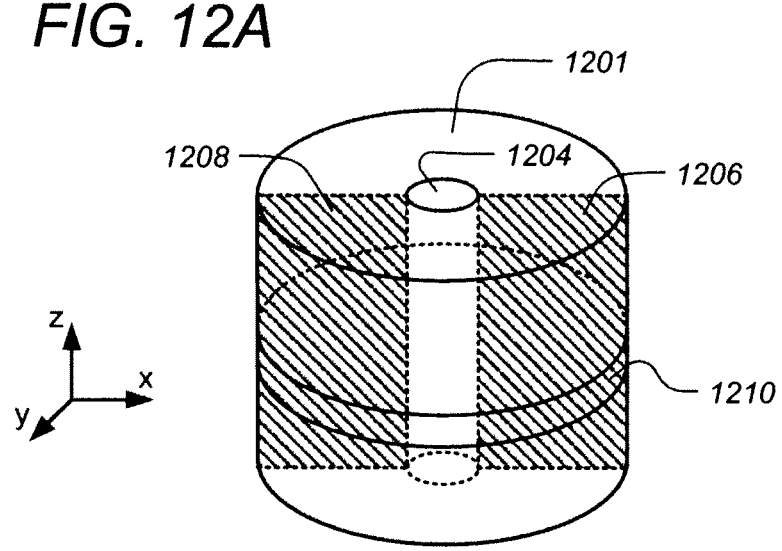
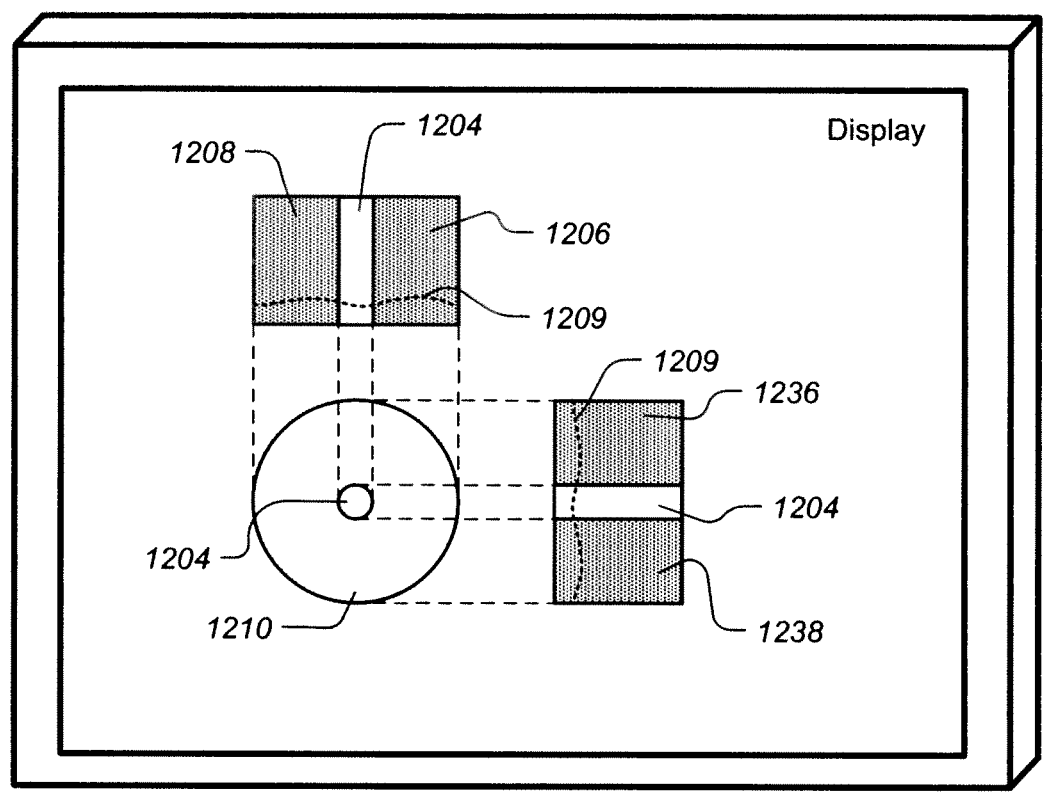
FIG. 12B

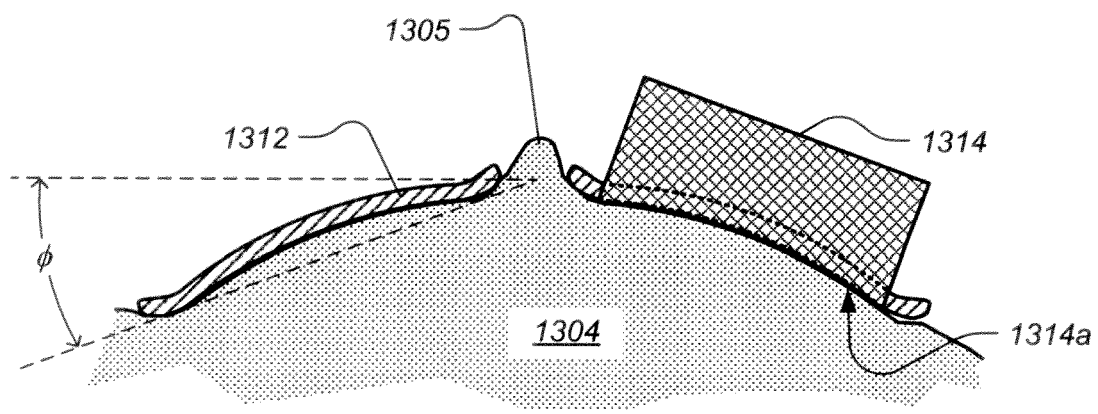
FIG. 13A
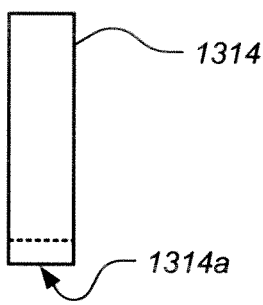 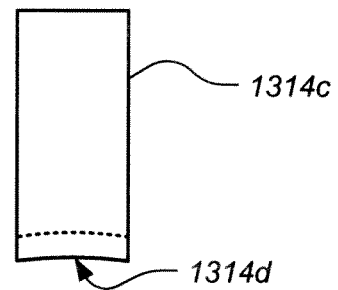
FIG. 13B    FIG. 13C

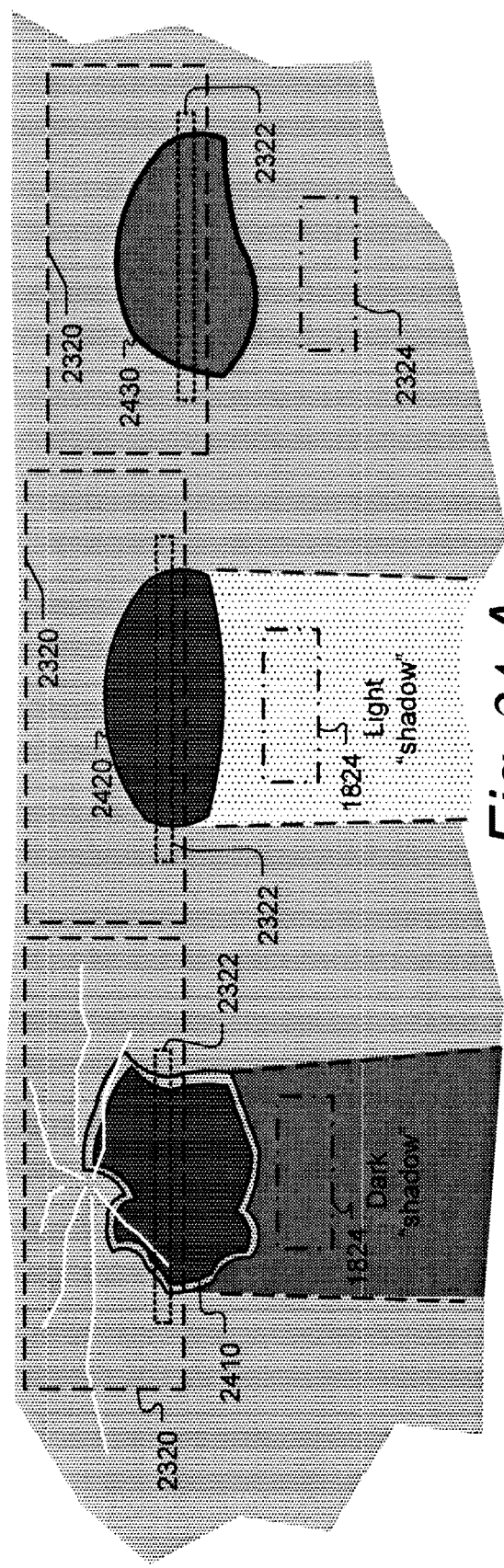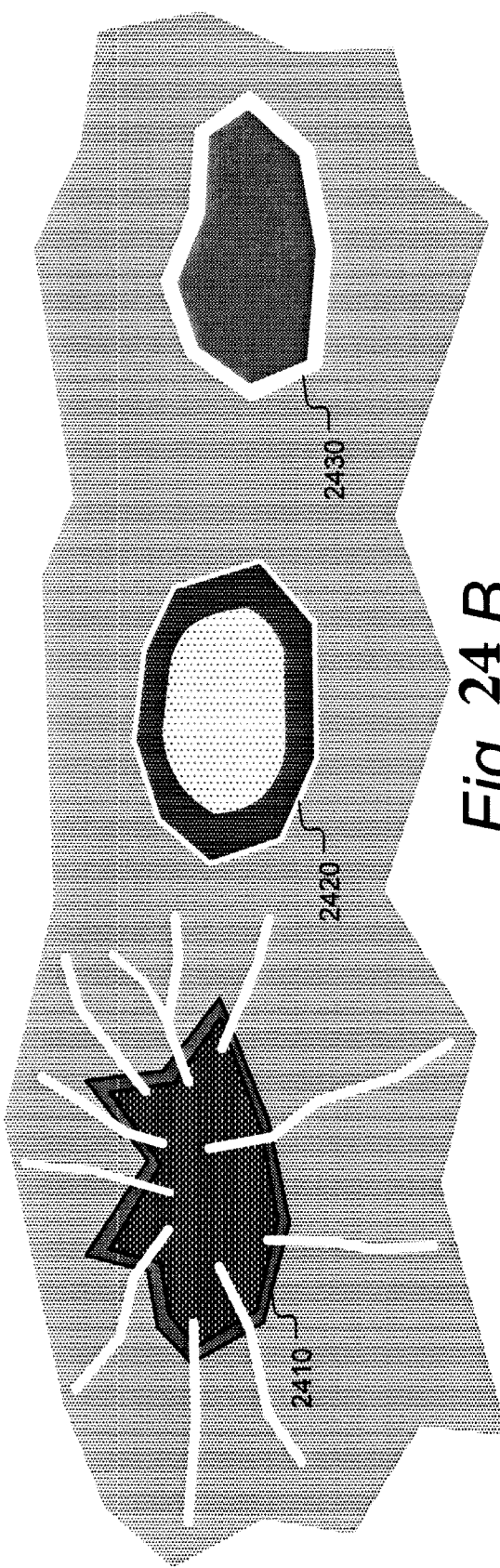
Fig. 24 A
Fig. 24 B

AUTOMATED BREAST ULTRASOUND EQUIPMENT AND METHODS USING ENHANCED NAVIGATOR AIDS

REFERENCE TO RELATED APPLICATIONS

This new filing is a divisional application of U.S. Ser. No. 16/667,526, filed Oct. 29, 2019, which is about to be patented. This application is a continuation of U.S. Ser. No. 15/716,650, filed on Sep. 27, 2017, which is a continuation of U.S. Ser. No. 14/455,408, filed Nov. 6, 2014, (now U.S. Pat. No. 10,251,621, issued on Apr. 9, 2019), which is a continuation-in-part of (i) International Application No. PCT/US14/67758, filed on Nov. 26, 2014 and (ii) U.S. Ser. No. 14/448,607, filed on Jul. 31, 2014, which is now U.S. Pat. No. 9,439,621, issued Sep. 13, 2016.

U.S. Ser. No. 14/448,607 claims the benefit of U.S. Provisional Application No. 61/910,139, file on Nov. 29, 2013, and U.S. Provisional Application No. and U.S. Provisional Application No. 62/003,448, filed on May 27, 2014, and is a continuation-in-part of I International Application No. PCT/US14/48897, filed Jul. 30, 2014, and (II) U.S. Ser. No. 14/084,589, filed Nov. 19, 2013.

U.S. Ser. No. 14/084,589 is continuation-in-part of U.S. Ser. No. 14/044,842, filed on Oct. 2, 2013 (now U.S. Pat. No. 9,826,958 issued on Nov. 28, 2017), which claims the benefit of U.S. Provisional Application No. 61/709,136, filed Oct. 2, 2012; U.S. Provisional Application No. 61/728,166, filed on Nov. 19, 2012; U.S. Provisional Application No. 61/830,241, filed on Jun. 3, 2013, and U.S. Provisional Application No. 61/680,900, filed on Jul. 31, 2013, and is a continutation-in-part of U.S. Ser. No. 12/289,371, filed Jul. 19, 2010. The entire contents of each of the reference's applications are hereby incorporated by reference.

FIELD

This patent specification relates to breast ultrasound equipment and methods that produce and use whole-breast navigator aids and pop-ups that improve the operation and results of medical ultrasound systems. One of the objectives is to speed up acquiring ultrasound measurements, reduce the time to find breast abnormalities while improving accuracy, and generally improve patient flow and accuracy of results. The equipment and methods are particularly helpful for women with breasts that are relatively dense to x-rays and therefore may not be screened, diagnosed, or treated as effectively with the use of standard x-ray mammograms.

BACKGROUND

In the US, the expected statistical figures for breast cancer in 2013 are estimated at approximately 230,000 new cases and 40,000 deaths. The mortality rate can be lowered if breast cancer could be detected in an earlier stage. Screening with X-ray mammography has been the gold standard for early detection of breast cancer. However, it is believed that in about 40% of the screening population typically more than 50% of their breasts are made up of dense fibroglandular breast tissues that tend to obscure abnormalities in X-ray mammograms. Recent clinical studies report that this "dense breast" gap could be economically and sufficiently dealt with using breast ultrasound. Currently, an automated-scan breast ultrasound system that received USFDA approval for breast cancer screening uses a chestward compression automated scanning procedure with an ultrasound transducer contacting the breast through a membrane. Such system is available from GE Healthcare under the name Invenia ABUS, and a similar system is believed available at least in Europe from Siemens Healthcare. A breast ultrasound system using scanning that is partly automated and partly manual, where the transducer contacts the breast through a camisole and a nipple pad, is reported by SonoCine, Inc. of Reno, NV. A system in which the transducers are acoustically coupled with the breast through a liquid and produces CT-like slice images of the breast, is reported by Delphinus Medical Technologies, Inc. of Plymouth, MI.

There are two major challenges facing practical breast cancer screening modalities. The first is cost, which can be measured as the cost of the actual examination and assessment of the results, and as the cost per detected cancer. Since breast cancer has low prevalence rate such that one cancer is generally found in 200 to 300 asymptomatic patients screened, the per patient screening cost must be kept low, currently typically to the range of $100-$200 in the U.S., in order to achieve a reasonable cost per cancer detected (i.e. $20,000 to $60,000 range). This cost range generally translates to limiting typical reading/interpretation time to about 3 minutes per patient, using an automated scanning system with a throughput of over 2,000 patients per year. For standard screening x-ray mammography, where only 4 new images are generated per patient at a screening examination in typical U.S. practice, this 3-minute interpretation time goal is relatively easily met. However, for current commercial breast ultrasound screening examinations, where hundreds or even thousands of new two-dimensional ("2D") thin-slice images per patient are obtained under chestward compression, in planes transverse to the coronal plane (often called "original" images), the goal of 3 minutes of reading/interpretation time is difficult to meet. An associated reading method can be used by configuring the original thin-slice images first into coronal thin-slice images and then into composite coronal thick-slice images, e.g., 2-30 coronal thin-slice images into one thick-slice image, so that a user can better search for abnormalities and better manage the reading/interpretation time. See for example U.S. Pat. No. 7,828,733, where the coronal thick-slices method is discussed. However, this method is still not quite fast enough, nor does it satisfactorily solve the "oversight" challenge described immediately below.

The second major challenge of breast cancer screening is "oversight," i.e., overlooking obvious cancers. A delay in cancer detection due to oversight can cause the cancer to progress to a more advanced stage resulting in decreased patient survivability and increased treatment cost. This problem is particularly serious when health professionals attempt to read/interpret breast images quickly. A study on blind re-reading of 427 prior screening x-ray mammograms, which were taken a year before the cancer detection, published in Radiology (by Warren-Burhenne, et al., 2000, Vol. 215, pages 554-562), reports that as many as 115 (or 27%) of the cancers could have been detected a year earlier and should be classed as oversights. In order to reduce the oversight problem, commercial computer-aided diagnosis ("CAD") systems have been developed for X-ray mammography screening. Development of clinically useful x-ray mammography CAD was no trivial matter, as the CAD must achieve sensitivity close to that of human readers. The development was undertaken by several commercial firms, some in collaboration with universities and national laboratories, over many years, and is believed to have consumed over $100 million in combined developmental cost. The CAD's impact in x-ray mammography is clearly visible—after 10 years of its commercial introduction, as reported by a study published in JACR (by Rao et al., 2010, Vol. 7, pages 802-805), by year 2008 75% of the screening x-ray mammograms were read with CAD assistance.

In the known commercial automated 3D breast ultrasound systems, the ultrasound beam is generally directed chestwardly during the scan while the breast is generally compressed chestwardly down. This method has significant advantages over the earlier non-chestward-compressed ultrasound scanning method proposals, such as a method that clamps the breast between vise-like scanning plates, as in standard x-ray mammography. The advantages of chestward scanning include: improved patient comfort, lesser depth of breast tissue that needs to be imaged during the scan, and the possibility of employing higher ultrasound frequency resulting in greater image quality. This is discussed in more detail in U.S. Pat. No. 7,828,733. A composite coronal thick-slice method (2-20 mm in slice thickness), which could be used as a guide or road map to aid the search for abnormalities, is also discussed in U.S. Pat. No. 7,828,733, as is the possibility of a full-breast composite image 2502 that preferably is a CAD enhanced expression of the sonographic properties of substantially all of the tissue imaged by the volumetric ultrasound scans, and of enhancing lesions according to their likelihood of malignancy (or another metric of interest). The thick-slice coronal image has proven helpful as a road map in current commercial automated 3D breast ultrasound systems. In commercial systems, a popular slice thickness of the coronal thick-slice image is believed to be 2 mm, which is selected for reasons of good image quality and less chance to miss smaller lesions or abnormalities. Slice thicknesses down to 0.5 mm also are believed to be used.

In known commercial automated 3D breast ultrasound screening systems using chestward compression scans, for each patient, several scans are typically made on each breast, for example 2-5 scans, although in some cases it can be a single scan and in some cases more than 5 scans. Each typical scan generates about 300 new images. Thus, 1,200 to 2,400 or more new images can be generated for each patient. With the manifold, e.g., 300- to 600-fold increase in the number of new images over screening x-ray mammography, readers can encounter even more oversights than the 27% or so that can be encountered in screening x-ray mammography. Thus, there is a need for efficient methods and systems to better manage both the reading/interpretation time as well as the oversight problem before breast ultrasound screening can be even more broadly employed to help more women.

Since the worldwide introduction of automated 3D breast ultrasound using chestward compression several years ago, radiologists at hundreds of facilities around the world have been struggling to read/interpret the huge volume of breast ultrasound images per patient study. At the present time, it is believed that only the best readers, even using the known composite 2 mm coronal thick-slice images as road maps, are able reach the 3 minutes practical goal per patient, while the majority of the readers are averaging more than 5 to 8 minutes per patient. No published studies are known on the "oversight" in current commercial automated 3D breast ultrasound, but one could guess that the oversight rate would not be below that found for screening mammography, i.e., the reported 27%.

The subject matter claimed herein or in a patent issuing from this patent specification is not limited to embodiments that solve any particular disadvantages or that operate only in environments such as those described above. Rather, this background is only provided to illustrate one exemplary technology area where some embodiments described herein may be practiced.

All the publications, including patents, cited throughout this patent specification, are hereby incorporated by reference.

SUMMARY

This patent specification relates to ultrasound examination of patients' breasts in which one or more ultrasound transducers scan a breast to derive measurements of ultrasound response along many planes that extend in chestward directions, the resulting measurements construct a 3D representation of scanned tissue that is enhanced to highlight and characterize likely malignancy and is presented and used in ways that particularly efficaciously addresses the time goal and the oversight problems discussed above.

According to some embodiments, an ultrasound transducer scans a breast with an ultrasound transducer that moves over the breast in a rotary or linear motion that preferably is automated but can be partly or in some cases mostly or fully manual. The transducer sends ultrasound energy into the breast and receives ultrasound energy modulated by patient's tissue. The resulting measurements of received ultrasound energy produce raw ultrasound images that typically are in planes transverse to the patient's chest wall, such as images in axial or sagittal planes. Through processing in specialized computer equipment, these raw images are transformed into a 3D representation of scanned tissue, with a value for each voxel of tissue in the 3D representation. Computer equipment uses this 3D representation of scanned tissue to produce ultrasound images that conform to planes that are generally parallel to the patient's chest wall, e.g., images conforming to coronal planes, each typically representing a slice of scanned tissue that is 2-20 mm thick in the chestward direction. A typical thickness is 2 mm, although thicker or thinner slices can be used.

Specialized computer equipment uses the 3D representation of scanned tissue, or representations derived from it, to facilitate faster and more reliable discovery of important abnormalities in the scanned tissue and of important characteristics of such abnormalities such as whether they are likely malignant or non-malignant. The system thus efficaciously addresses the challenges of rapidly acquiring the necessary measurements and addressing the issues of a realistic time goal for assessing the scan results and of reducing oversight errors.

In one example, a system for ultrasound examination of a patient's breast comprises an ultrasound transducer compressing an upwardly facing patient's breast chestwardly down and scanning the breast through a gel-impregnated fabric in a scanning motion relative to the breast while sending ultrasound energy into the breast and receiving ultrasound energy from scanned tissue thereby producing ultrasound responses for breast slices that conform to planes extending down in chestward directions; a computer-driven scan controller mechanism and a linkage between the controller mechanism and the ultrasound transducer, configured to control the scanning motion of the transducer relative to the breast; a first programmed computer processor module coupled with the transducer to receive the ultrasound responses therefrom and configured to apply computer processing thereto producing a three-dimensional (3D) structure representing sonographic response characteristics of volume elements (voxels) of scanned tissue; a second programmed computer module configured to apply computer processing algorithms to the 3D structure to segment out influences of selected scanned tissue and to find tissue abnormalities in the remaining whole-breast 3D structure; a third programmed computer module configured to produce enhancements of at least some of the found tissue abnormalities; a fourth programmed computer module configured to produce a whole-breast navigator structure depicting the scanned breast and abnormalities therein that have been enhanced by the third programmed computer module; and a computer display configured to produce and display a depiction of the whole-breast navigator structure with abnormalities therein enhanced by the fourth programmed computer module, and respond to user input regarding an abnormality in the whole-breast navigator structure by producing and concurrently displaying pop-up depictions of the abnormality as it appears in a coronal thick-slice image of the scanned tissue that has a selected thickness and in at least one thin-slice chestwardly oriented image. The scan controller mechanism and the linkage are configured to compress the breast with an essentially planar template rotating relative to the breast and to scan the breast with the ultrasound transducer in a rotary scan pattern. The third programmed computer module is configured to boost representations of found tissue abnormalities by making likely malignant abnormalities darker or lighter in the navigator structure than if not boosted; to boost representations of abnormalities that represent likely speculations in the navigator structure; to boost representations of abnormalities that represent a likely cyst and enhance an image of a cyst in the displayed navigator structure by placing a spot therein that differs from a remainder of the cyst image; and to detect and remove influences of ultrasound responses resulting from poor ultrasound transducer-to-breast coupling. The fourth programmed computer module is configured to produce the whole-breast navigator structure through a process comprising assigning to a pixel in a projection of the navigator structure a value related to the darkest voxel value in a related column of voxel values; to produce the whole-breast navigator structure through a process comprising assigning to a pixel in a projection of the navigator structure a value related to voxel values along a stretch of 1-3 mm containing the darkest voxel values of a related column of voxel values; and/or to produce the whole-breast navigator structure through a process comprising assigning to a pixel in a projection of the navigator structure a value related to only some of the voxel values of a related column of voxel values.

The detailed description below together with the drawing figures presents other embodiments and variations.

BRIEF DESCRIPTION OF THE DRAWINGS

To further clarify the above and other advantages and features of the subject matter of this patent specification, specific examples of embodiments thereof are illustrated in the appended drawings. It should be appreciated that these drawings depict only illustrative embodiments, and are therefore not to be considered limiting of the scope of this patent specification or the appended claims. It should also be appreciated that components or steps illustrated in one of the drawings can be used together with or instead of components or steps illustrated in one or more other drawings within the scope of the disclosed embodiments. The subject matter hereof will be described and explained with additional specificity and detail through the use of the accompanying drawings in which:

FIG. 2 illustrates in a perspective exploded view an essentially planar scanning template and an ultrasound transducer for scanning a chestwardly flattened breast in an automated scan pattern.

FIG. 3A is a top plan view of an essentially planar scanning template; FIG. 3B is a cross-section through lines A-A', and FIG. 3C is a cross-section through lines B-B'.

FIG. 12A illustrates a 3D scanned breast volume and its relationship with original 2D scanned slices; FIG. 12B illustrates a display of a coronal slice and associated orthogonal views of original 2D scans.

FIG. 13A illustrates a cross-section of breast being scanned with an ultrasound transducer that has a curved concave lower side and scans through an opening in a template that can be essentially planar or spherical or otherwise curved in two dimensions with a departure angle greater than 2.5°; and FIGS. 13B and 13C illustrate side views of ultrasound transducers according to some embodiments.

FIGS. 24A and 24B illustrate other examples of enhancements, including of representations of masses and speculated abnormalities in a breast.

DETAILED DESCRIPTION

Several devices and methods of acquiring breast sonographic measurements are discussed in detail below, then there is a discussion of using these measurements to produce enhanced navigator aids and associated pop-ups.

Figure 1A:
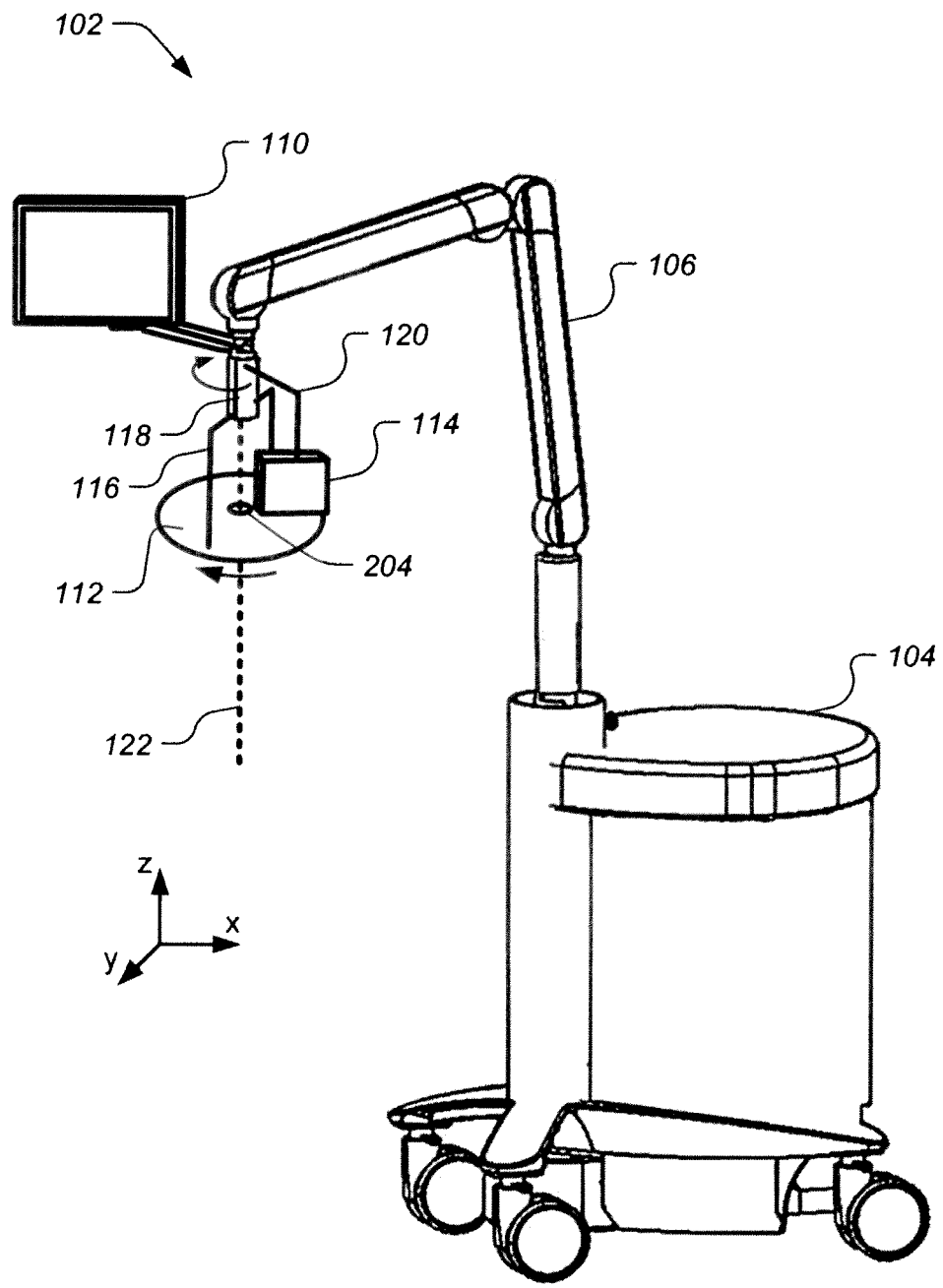
FIG. 1A illustrates in a perspective view a full-field automated breast ultrasound (FFBU) device.

FIG. 1A illustrates a perspective view of a full-field breast ultrasound (FFBU) scanning apparatus 102 according to a preferred embodiment, comprising a frame 104 that typically contains an ultrasound processor, a movable support arm 106, and a monitor 110 connected to the support arm 106. FFBU scanning apparatus 102 further comprises an essentially planar radial scanning template 112 and an ultrasound transducer 114. Radial scanning template 112 is configured to chestwardly compress down a breast of a patient (e.g., a supine patient) while rotating around an axis 122, preferably centered on a nipple hole 204. The ultrasound transducer 114 rotates with the radial scanning planar template 112 and scans the breast through a slot-shaped, radially extending opening therein. Typically, the equipment is provided with several interchangeable scanning templates that differ in size and/or shape to fit different patient anatomies and scanning techniques or ultrasound modes.

Figure 1B:
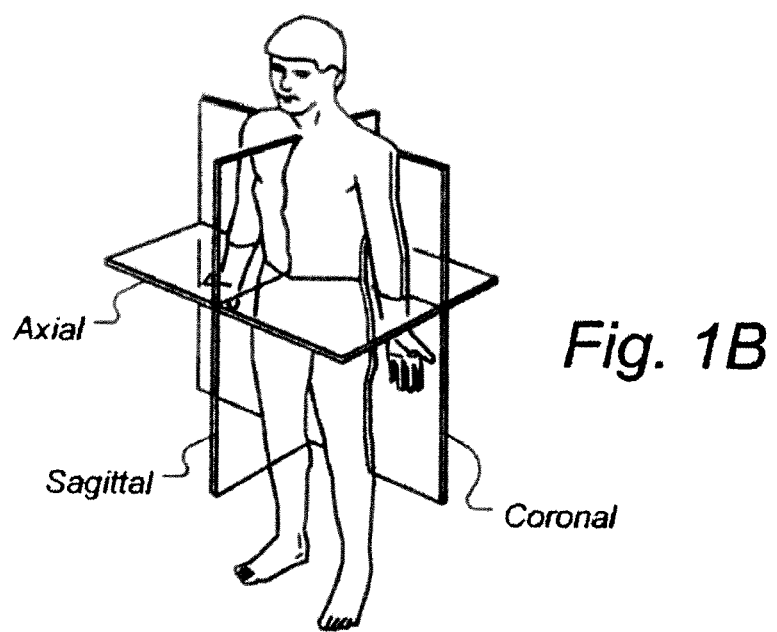
FIG. 1B illustrates a convention for naming planes relative to a patient's body.

For reference purposes, in this patent specification the +z direction refers to an outward direction away from the patient's chest, the x-axis refers to a left-right direction relative to a supine patient, and the y-axis refers to a head-to-toe direction. The x-y plane thus corresponds to a coronal plane of a breast, the x-z plane corresponds to an axial plane, and the y-z plane corresponds to a sagittal plane. FIG. 1B illustrates the relevant coronal, axial and sagittal planes. This specification also refers to chestward directions, which include the (−z) direction and more generally directions toward the chestwall of a patient.

Also illustrated in FIG. 1A is a rigid, two-pronged connector 116 and a rigid, single-arm connector 120 that mechanically or electro-mechanically or otherwise connect the radial scanning template 112 and the ultrasound transducer 114, respectively, to an actuator assembly 118 for achieving the movement functionalities described herein. The elements 116-120 in FIG. 1 are drawn by way of a conceptual example only and not to scale. In view of the disclosure in this patent specification, a person skilled in the art would be readily able to construct the various mechanical/electrical or other linkages, actuators, motors, sensors, etc., required to achieve the described mechanical functionalities without undue experimentation. Accordingly, such mechanical/electrical or other details are mostly omitted from the drawings herein for clarity of description. The actuator assembly 118 can be computer-controlled to achieve the required scanning motion of template 112 and transducer 114, and can be referred to as a computer-driven scan controller mechanism. Connectors 116 and 120 can be referred to as a linkage or linkage mechanism.

Preferably, support arm 106 is configured and adapted such that the overall compression/scanning assembly 112-120 (i) is neutrally buoyant in space, or (ii) has a light net downward weight (e.g., 2-3 pounds) for breast compression, while allowing for easy user manipulation. Optionally, the support arm 106, the template, and/or the transducer(s) can comprise potentiometers and/or other sensors (not shown) to allow force, position, and/or orientation sensing for the overall compression/scanning assembly 112-120, the template, and/or the transducer(s). Other types of force, position, and/or orientation sensing (e.g., gyroscopic, magnetic, optical, radio frequency (RF)) can be used instead or in addition.

Within frame 104 there can be provided a fully functional ultrasound engine for driving one or more ultrasound transducers and generating volumetric breast ultrasound measurements and images from the scans in conjunction with the associated position and orientation information regarding transducer 114. The volumetric scan measurements can be transferred to one or more other computer systems for further computer-processing using any of a variety of transfer methods known in the art. A general purpose computer, which can be implemented on the same computer equipment set as the ultrasound engine, can be provided for general user interfacing and system control. The general purpose computer can be a self-contained stand-alone unit, or can be remotely controlled, configured, and/or monitored by a remote station connected across a network.

FIGS. 2, 3A, 3B, and 3C illustrate more detailed views of an essentially planar radial scanning template 112 in accordance with an example of a disclosed embodiment. Radial scanning template 112 preferably is rounded, e.g., has a generally circular shape though the shape can be rounded without being circular, and defines therein a slot-shaped opening 202 that extends generally radially from a central opening 204. The slot-shaped opening 202 is dimensioned to allow ultrasound transducer 114 to scan the breast with ultrasound through opening 202 while compressing the breast. Although shown as a one-dimensional array in FIG. 2, the ultrasound transducer 114 more generally can be multiple-arrayed (sometimes referred to as 1.25D, 1.5D, 2D, etc.), or hybridizations thereof without departing from the scope of the disclosed embodiments. In one embodiment, the FFBU scanning apparatus 102 is provided with an interchangeable (and/or disposable) set of essentially planar radial scanning templates 112 that are differently sized or shaped for differently-sized or shaped breasts. In one example, eight (8) different radial scanning templates having base diameters of 4 inches, 5 inches, 6 inches, 7 inches, 8 inches, 9 inches, 10 inches and 12 inches are provided. Exemplary diameters for the central opening 204 range between about 0.25" to 1" (0.25 inches to 1 inch). The slot-shaped opening 202 may have a width typically in the range of 0.25" to 1" depending on the size of the ultrasound transducer to be used therewith. In addition, a selection of templates can be provided that are not essentially planar but have greater departure angles.

In one example, the ultrasound transducer 114 is supported and/or actuated independently of the radial scanning template 112. In another embodiment, the ultrasound transducer 114 is integral with, clipped to, or otherwise secured to or fused with or mounted on the radial scanning template 112 for joint support and/or actuation.

Referring to FIG. 3A, the essentially planar radial scanning template 112 is shaped as a circular plate having a circular hole 204 located at the center of the circular plate 304 and a radially extending slot-shaped opening 202 from near the hole 204 to near the periphery of plate 304. FIG. 3B illustrates a sectional view along lines A-A', and FIG. 3C illustrates a sectional view along lines B-B.

In one example, the radial scanning template 112 is formed of a transparent or at least translucent material having mechanical properties similar to those of 40-mil thick polycarbonate plastic, 40-mil polystyrene plastic, or a mechanically equivalent thickness of polyethylene terephthalate (PETE) plastic. In this embodiment, there is some amount of "give" or flexibility to the template 102, providing some degree of comfort to the patient as well as adaptability to differently-sized breasts while at the same time providing for substantial stabilization of the breast tissue for reliable volumetric imaging of the breast. Such a template is called "semi-rigid" in this patent specification. In another embodiment, the material for template 102 comprises a transparent or at least translucent material such as 140-mil thick glass, 140-mil acrylic, or 140-mil polycarbonate plastic. Such a template is called "rigid" in this patent specification. Preferably, a lower surface of the radial scanning template 112 makes a slippery contact with the skin surface in the presence of an ultrasound couplant such as gel between the template and the breast so that rotation is easily achieved even when the breast is under some degree (e.g., 4-12 lbs.) of downward compression. Despite the slippery contact with the breast, stabilization is provided by virtue of the generally circular shape of the radial scanning template 112. Preferably, a curled lip, e.g., as illustrated in FIG. 3B at 304A, is provided around the periphery 304 as well around the central hole 204 as illustrated at 204A, and a similar curled lip is provided at the edges of slot-shaped opening 202 as illustrated in FIG. 3C at 202a, to prevent skin cuts or chafing and provide additional comfort to the patient, similar to the way curled upper lips are provided on many paper, polystyrene, and PETE plastic drinking cups.

Figure 4A:
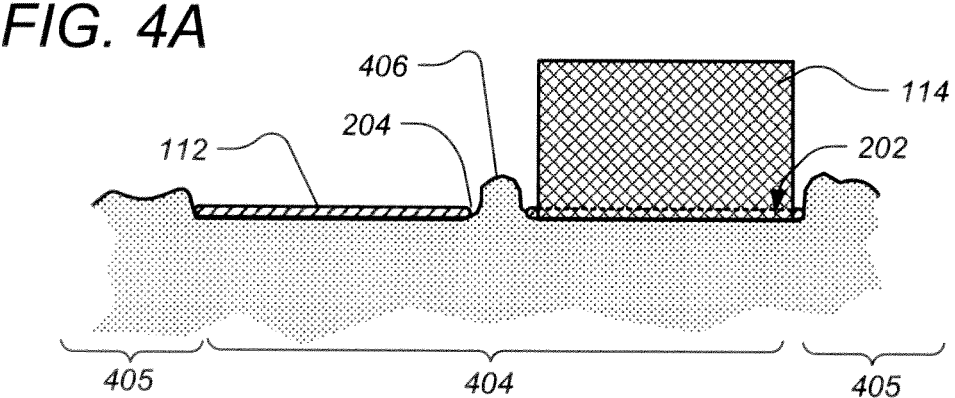
FIG. 4A is a cross-sectional view illustrating a patient's breast that is chestwardly compressed with an essentially planar template and is being scanned with an ultrasound transducer through a radially extending opening in the template.
Figure 4B:
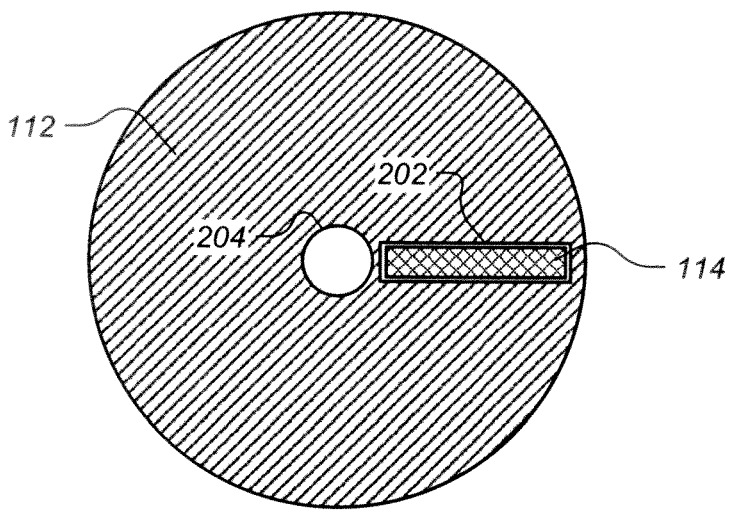
FIG. 4B is a top view of the template of FIG. 4A.
Figure 4C:
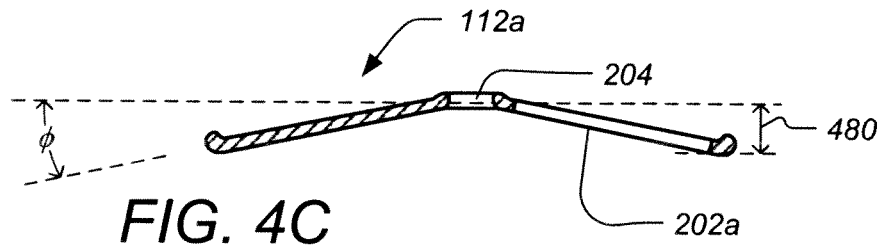
FIG. 4C is a cross-sectional view a scanning template that is otherwise similar to the template of FIGS. 4A and 4B but departs from absolute planarity by a departure angle φ that is greater than 2.5°.

FIG. 4A illustrates a side cut-away view of the essentially planar radial scanning template 112 as it chestwardly compresses down a breast 404 having a nipple 406. The view can correspond to the axial or sagittal plane, and also illustrates patient tissue 405 that surrounds breast 404 laterally (e.g., in the coronal plane). The nipple 406 protrudes through the central opening 204. The transducer 114 scans the breast 404 through the slot-shaped opening 202. FIG. 4B illustrates a top conceptual view of FIG. 4A. FIG. 4C illustrates a template 112A that can be otherwise similar to the essentially planar template 112 but has a conical surface that departs from absolute planarity by a departure angle φ (phi) that is greater than 2.5°. Rather than shaped as a truncated cone, template 112A can be shaped as a shallow inverted bowl with a side curving in two orthogonal dimensions. A template with a departure angle φ greater than 2.5° can be used, if desired, in place of each of the essentially planar templates illustrated and discussed in this patent specification.

Whenever a departure angle is used that moves away from 0°, there is a penalty of scanning through increased breast thicknesses, which is measured as the distance from the scan surface to the chest wall. For example, if we define t (distance 480 in FIG. 4C) as the maximum differential thickness increase from the scan surface to the chest wall surface, then t could be expresses as the radial length of the transducer L times the sin Φ (phi) (the departure angle):

$$t = L \sin \Phi$$

The following table shows the relationship:

TABLE 1

| Φ (degree) | Sin Φ | L = 3 inch t (cm) | L = 4 inch t (cm) |
|---|---|---|---|
| 5 | 0.0872 | 0.7 | 0.9 |
| 10 | 0.1736 | 1.3 | 1.8 |
| 15 | 0.2588 | 2.0 | 2.6 |
| 20 | 0.3420 | 2.6 | 3.5 |
| 25 | 0.4226 | 3.2 | 4.3 |
| 30 | 0.5000 | 3.8 | 5.1 |

At 10 MHz, according to D'Astous and Foster (Ultrasound in Med. & Biol., 1986, Vol. 12, pages 795-808), an increase in 2.5 cm in scan depth would increase attenuation by 25 to 50 dB, which could have a serious negative impact on image quality. Unless in extraordinary circumstances, either due to breast size or shape, where larger departure angles may need to be used, for transducers having a radial length smaller than three inches, one should preferably consider using a departure angle of less than 30 degrees. For a three-inch transducer, one should preferably use a departure angle of less than 20 degrees. For a four-inch transducer, one should preferably use a departure angle of less than 15 degrees.

In the particular embodiment of FIGS. 4A and 4B, the slot-shaped opening 202 and the ultrasound transducer 114 both extend along substantially the entire distance from the central nipple hole 204 to the periphery of the radial scanning template such that a complete volumetric scan can be achieved in a single 360-degree rotation, with optional beam-steering for facilitating sub-areola imaging. If desired, the rotation angle can be extended by a few degrees to achieve some overlap of scanned breast tissue and thus ensure complete coverage with no angular gaps.

Figure 5:
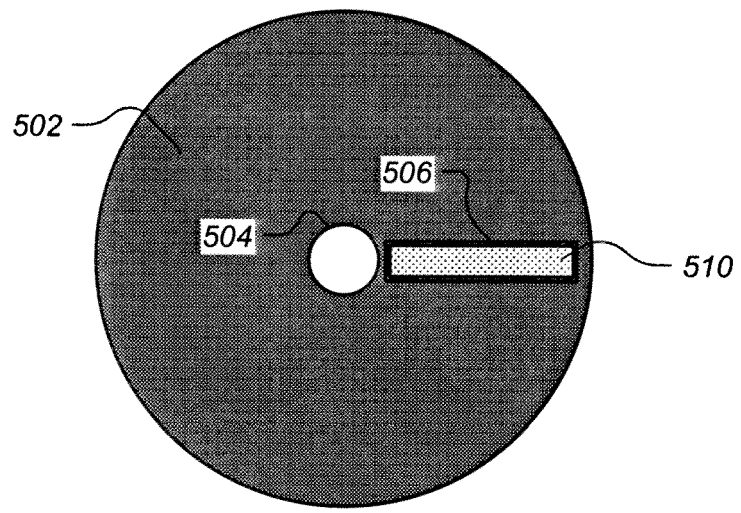
FIG. 5 is a plan view of a template with a membrane that is permeable to an ultrasound couplant such as a gel, through which an ultrasound transducer can scan the breast.

FIG. 5 illustrates a top view of a radial scanning template 502 according to one embodiment, comprising a central opening 504, a slot-shaped opening 506, and a membrane 510 extending across the slot-like opening 506. The ultrasound transducer (not shown in this figure) scans the breast through the membrane 510. The membrane 510 preferably comprises a fabric material porous to ultrasound coupling agent such as gel, which can be advantageous in that air bubbles are reduced. As used in this patent specification, fabric refers generally to a material structure of interconnected or interleaved parts, such as can be formed by knitting, weaving, or felting natural or synthetic fibers, assembling natural or synthetic fibers together into an interlocking arrangement, fusing thermoplastic fibers, or bonding natural or synthetic fibers together with a cementing medium, and further refers to materials having similar textures or qualities as those formed thereby, such as animal membranes or other naturally occurring substances having fabric-like properties (either inherently or by processing), and such as materials generated by chemical processes yielding fabric-like webbings. One particularly suitable material for the taut fabric sheet comprises a polyester organza material having a filament diameter of about 40 microns and a filament spacing of about 500 microns. However, the fabric membrane may comprise any of a variety of other fabrics that are substantially inelastic and generally porous to ultrasound couplants without departing from the scope of the present teachings. Examples include, but are not limited to, polyester chiffon fabrics and cloth fabrics comprising straight weaves of substantially inelastic fibers. If the weave is particularly tight, for example, as in cloth used in men's dress shirts or in many bed sheets, porosity can be achieved by additional treatment. The additional treatment can involve forming an array of perforations in the cloth or otherwise introducing irregularities that allow the ultrasound couplant to soak or seep through.

Figure 6:
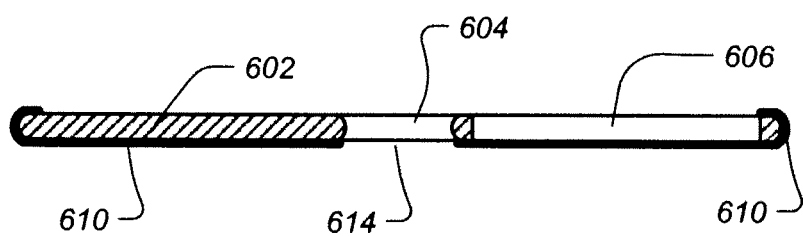
FIG. 6 is a cross-sectional view of the template of FIG. 5.

FIG. 6 illustrates a cross-sectional view of an essentially planar radial scanning template 602 according to one embodiment, comprising a central opening 604, a slot-shaped opening 606, and a porous fabric membrane 610 in the form of a stretchable, generally circular fabric sock extending over the entire bottom-side of the planar template 602 (i.e., the side that faces and contacts the patient's breast) and across the slot-shaped opening 606 but preferably with a central hole 614 in the membrane for the nipple to protrude through. The sock can but need not extend over some or all of the upper side of template 602. According to another embodiment, the porous fabric sock can be mounted on a circular or round frame that is snapped on or otherwise secured to the substantially planar radial scanning template 602. The ultrasound transducer (not shown in this figure) scans the breast through the porous fabric membrane 610 wetted with an acoustic coupler such as gel. In this example, the template with the fabric sock and the transducer all rotate relative to the breast. As discussed in another example below, an alternative is to compress the breast with a membrane such as gel-wetted fabric, compress the breast through the membrane, and rotate the template and transducer relative to the breast and the membrane.

Figure 7:
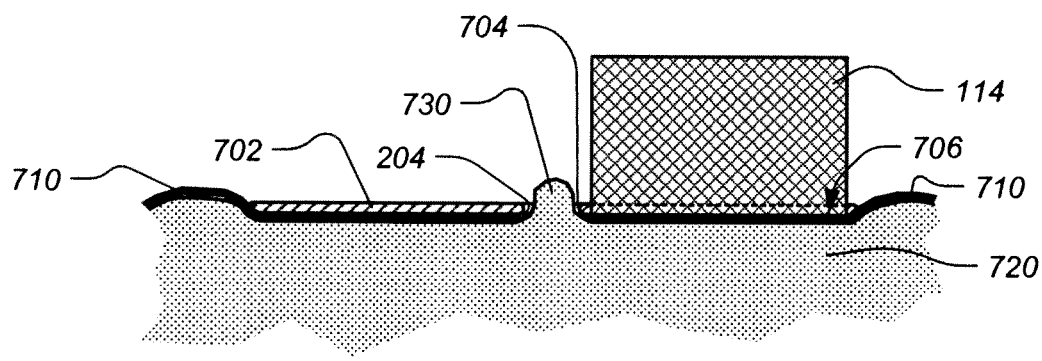
FIG. 7 is a cross-sectional view similar to FIG. 6 but additionally illustrating a portion of a breast being scanned and a scanning ultrasound transducer.

FIG. 7 illustrates a side view section of an essentially planar radial scanning template 702 according to a preferred embodiment, comprising a central opening 704, and a slot-shaped opening 706. The radial scanning template 702 is positioned over a patient (not shown except for a portion of the breast 720) wearing a brassiere-shaped or vest-shaped article 710 comprising a porous membrane such as fabric at least over the breast and preferably with a central hole 714 for the nipple 730 to protrude through. The ultrasound transducer 114 scans the breast through the porous fabric article 710.

Figure 8:
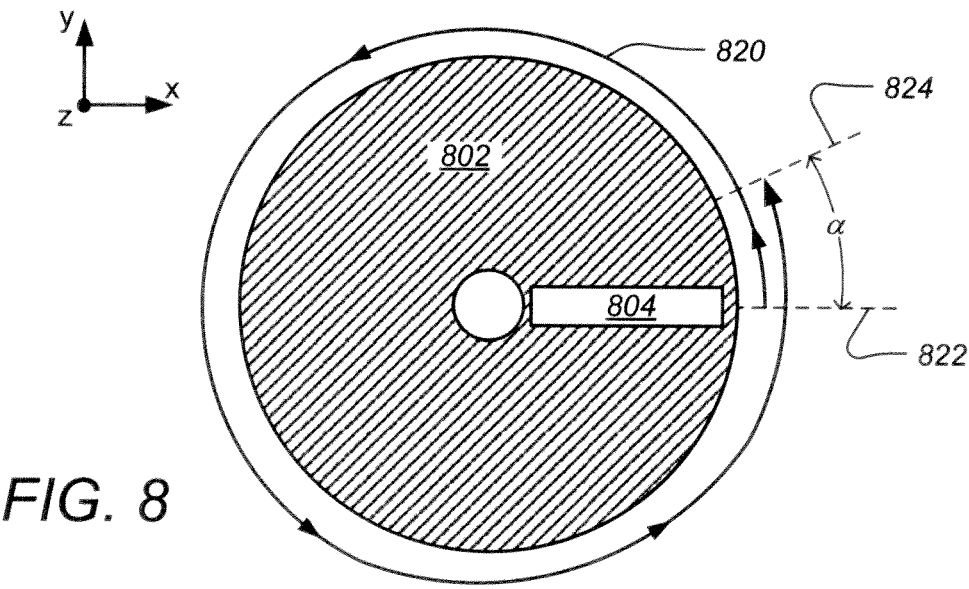
FIG. 8 is a top view of a template illustrating scan overlap angles.

FIG. 8 illustrates a top view of a radial scanning template 802 according to one embodiment, comprising a single slot-shaped opening 804 corresponding to a single ultrasound transducer (not shown in this figure). The radial scanning template is preferably rotated 360° plus an overlap angle α (alpha) during the breast ultrasound scan, the overlap angle (if desired) preferably being in a range of 5° to 45°. The coronal sector associated with the overlap angle alpha (i.e., the pie-shaped sector of the compressed breast subtending the arc between radial lines 822 and 824 in FIG. 8) is thus imaged twice. The dual volumetric images for the overlap sector can be advantageously used to reduce discontinuity artifacts in the volumetric representation of the breast that might otherwise occur along the radial line 822. In one embodiment, the dual volumetric images are arithmetically averaged for smoothing over the discontinuity. However, more advanced stitching techniques can be used. Other mathematical methods for processing the dual volumetric images for reducing discontinuity artifacts exist and are within the scope of the preferred embodiments. One non-limiting example is weighted averaging in which the weights applied to one of the images of the overlap gradually decrease from unity to zero from the start to the end of the overlap zone while the weights applied to the other image in the overlap zone gradually increase from zero to unity. For example, the weights applied to the image obtained at the start of the circular scan increase with angular distance from line 822.

Figure 9:
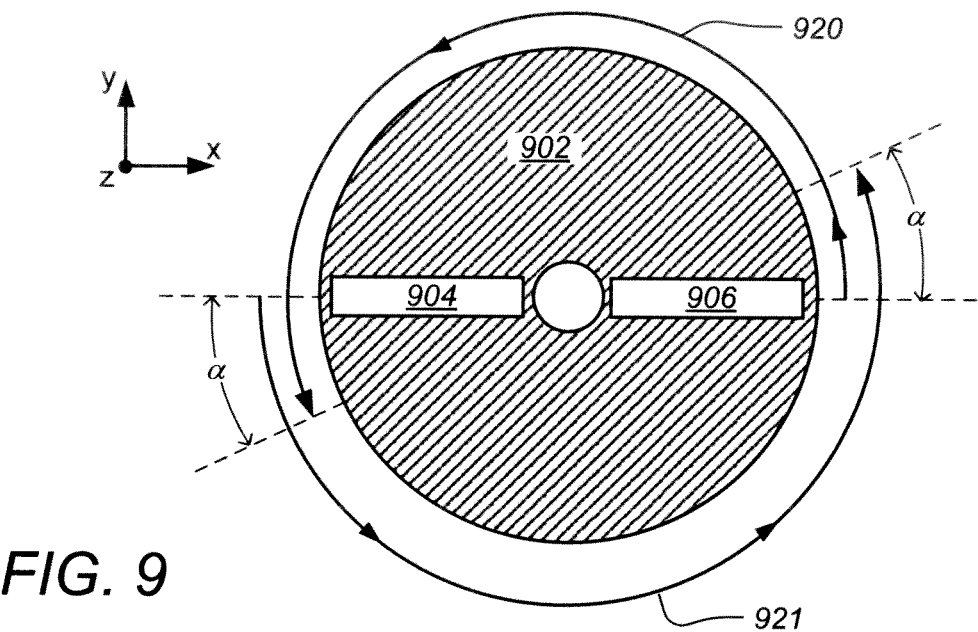
FIG. 9 is a top view of a template having two radial slots for two separate ultrasound transducers, according to some embodiments.

FIG. 9 illustrates a top view of a radial scanning template 902 according to one embodiment, comprising two slot-shaped openings 904 and 906 corresponding to two ultrasound transducers (not shown) used during a scan. In one preferred embodiment, the radial scanning template 902 is preferably rotated by 180° plus, if desired, an overlap angle a during the breast ultrasound scan, thereby reducing scanning time as compared to the use of a single ultrasound transducer. The scan images from the two transducers are processed through stitching, blending, or other competing algorithms into a volumetric image of the breast.

In another preferred embodiment, the radial scanning template 902 is rotated through the full 360°, plus an overlap angle if desired, with the different ultrasound transducers being differently configured with respect to at least one imaging parameter. The resultant volumetric scans are then compounded or composited in any of a variety of advantageous ways, with or without different weighing, and/or can be viewed as separate images. Parameters that can be varied among the transducers include, but are not limited to, scan frequency, tilt angle, elevation beamwidth, scan mode (e.g., B-mode, harmonic, Doppler, elastography), in-plane acoustic interrogation angles, and different in-plane multi-angle compounding schemes. It should be apparent to a person of ordinary skill in the art after having read this patent specification to expand this scan configuration using 2 transducers to a scan configuration using a greater number of transducers.

Figure 10:
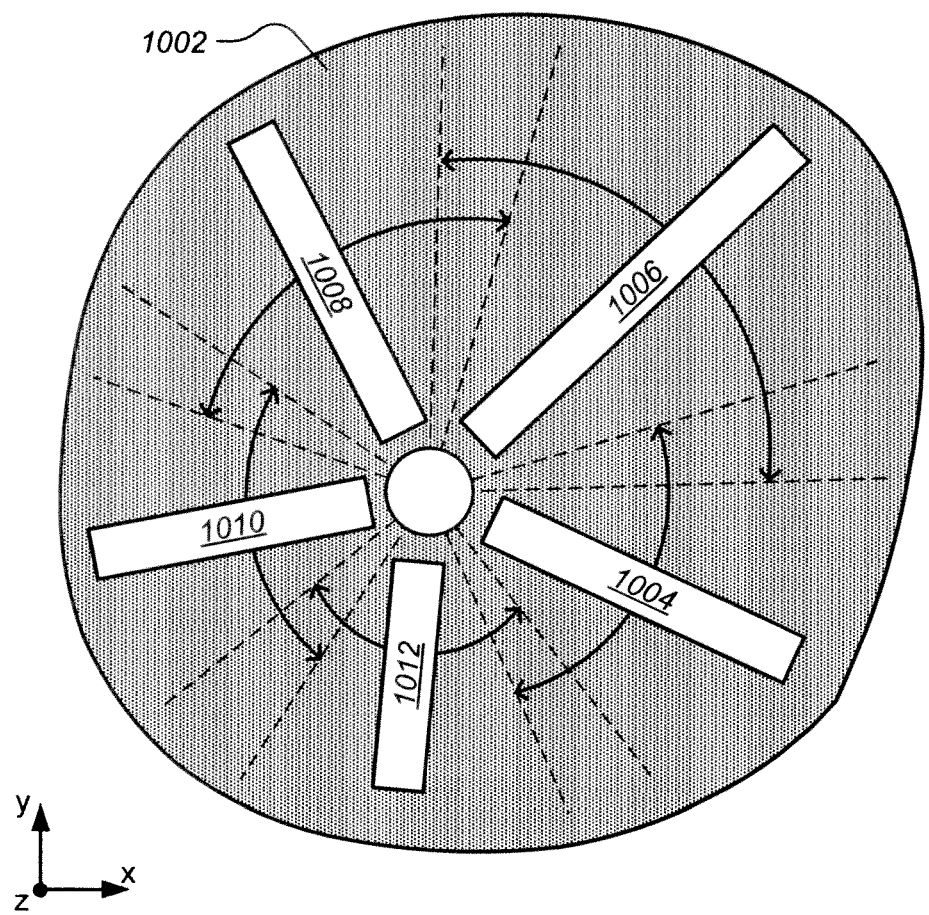
FIG. 10 is a top view of a template that has a non-circular outline and multiple radial slots through which respective transducers of different sizes and/or other characteristics scan a breast or at least respective sectors of a breast.

FIG. 10 illustrates a top view of a radial scanning template 1002 according to one embodiment, comprising five slot-shaped openings 1004, 1006, 1008, 1010, and 1012 corresponding to five ultrasound transducers (not shown in this figure), each scanning the breast through a respective one of the openings directly or through a membrane (fabric) as described for an individual transducer in other embodiments. According to the preferred embodiment of FIG. 10, at least two of the ultrasound transducers have different radial lengths corresponding to different distances from the central nipple hole to the periphery of the radial scanning planar template. Each ultrasound transducer scans a different coronal sector of the breast. In the example of FIG. 10, which is for the left breast of a supine patient, the longest ultrasound transducer 1006 scans the coronal sector nearest the axilla, while the shortest ultrasound transducer 1012 scans an inferior medial sector of the breast. Accordingly, it can be appreciated that the general shape of a radial scan template according to the disclosed embodiments is not limited to circular shapes with nipple openings at the geometric center, but rather includes different shapes and different locations of the nipple opening relative to the template's radial periphery. Likewise, a radial scan template according to the preferred embodiments is not limited to a circular shape, but rather can have a differently shaped periphery (e.g., oblong, elliptical, cam-shaped).

Figure 11A:
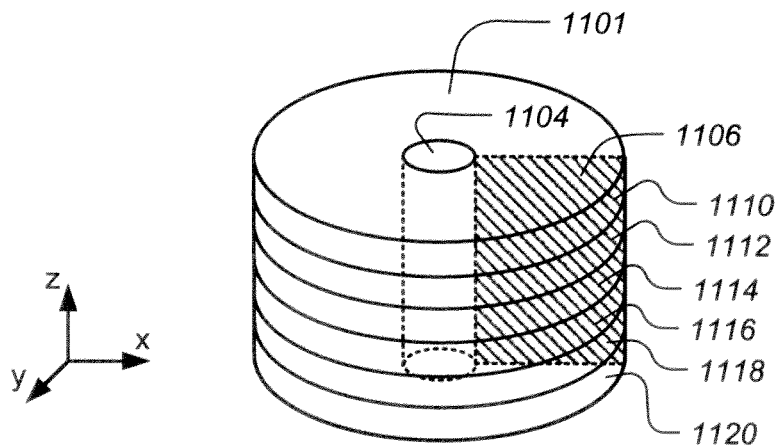
FIG. 11A illustrates a 3D scanned breast volume with coronal slices, according some embodiments.

The obtained ultrasound scans can be advantageously used in a variety of ways in accordance with the disclosed embodiments. For example, it has been found that the acquired volumetric measurements are particularly advantageous for generating coronal slice images of the breast as shown in FIG. 11A, each preferably representing a slice that has a selected thickness in the z-direction (i.e., a direction away from the patient's chest wall), although images of slices that have other orientations and may differ in thickness from each other also are with the scope of this patent specification. The slice thickness preferably is in the range of 0.5-2.0 mm, but can be in the range of 0.1-1.5 mm, or 0.1-2.0 mm, or 0.1-10.0 mm, and even a greater range. Another advantage of displaying coronal images is that they can show lesion spiculations well, which are a readily recognizable feature of a cancerous lesion.

Figure 11B:
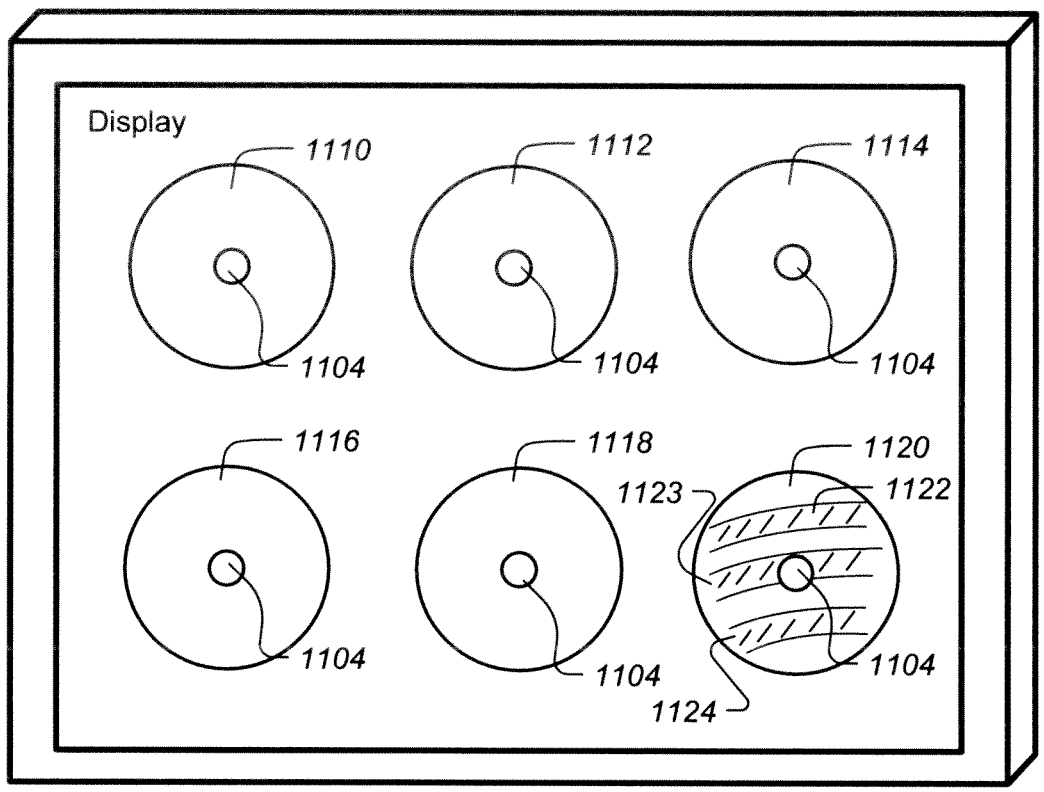
FIG. 11B illustrates a display of images of such coronal slices.

FIGS. 11A and 11B illustrate a 3D image 1101 of the breast represented as slices 1110-1120 reconstructed from 2D radial scan images such as image 1106, and the display of slice images 1110-1120 of slices of the 3D structure of breast voxel values. The 3D structure 1101 is reconstructed from a great number of original 2D images from the radial scan that are transverse to the coronal plane, e.g., they extend in chestward directions. One such original 2D image 1106 is shown. Also shown is the central nipple hole 1104. The 3D image 1101 can be considered as divided into images of coronal slices of the breast (slices perpendicular to the z-axis) 1110, 1112, 1114, 1116, 1118, 1120, etc., reconstructed from the volumetric stack 1101 as known the ultrasound imaging technology. FIG. 11B illustrates an example of how the slice images can be displayed to the physician or other health professional. The last (bottom) slice 1120 is usually the slice at the chest wall or rib cage (which generally would show ribs 1122, 1123, 1124, etc. to confirm that adequate breast penetration has been achieved). The nipple and sub-areola regions, obtained either through beam-steering or manual scanning with a handheld transducer or otherwise, can be displayed in stitched images or separately.

FIGS. 12A and 12B illustrate a single corona thick-slice slice image 1210 in a volumetric 3D image or stack 1201 of breast tissue, and thin-slice 2D images. Two original 2D radial scan images 1206 and 1208 bisect the 3D image, for example in a sagittal plane, and are spaced 180° from each other. Alternatively, the 2D radial scan thin-slice images can be at other chestward orientations. The central nipple hole 1204 is also shown. FIG. 12B illustrates a display of 2D images 1206 and 1208 together with a display of 2D images 1236 and 1238 that are a pair orthogonal to the pair 1206 and 1208 (e.g., if the pair 1206-1208 are sagittal images than the pair 1236-1238 are axial images). Chest wall line 1209 is also shown.

Notably, in this example the two orthogonal pairs of images are original 2D radial scan images, unlike similar pairs in known commercially available FFBUs, where orthogonal pairs are believed to be constructed from a volumetric reconstructed 3D image stack and consequently have reduced image quality. Coronal thick-slice images as shown in FIG. 11B can be reviewed quickly, and/or a cine or other review of the coronal image in FIG. 12B can be carried out, and/or a quick cine or other review of the original 2D images in FIG. 12B. One way to perform a cine review of the original 2D images is simply to rotate the coronal slice 1210 to view the 180° pairs. Rotation of the coronal slice can be done with a control knob, by a cine review control, or by another interface, while other information such as the rotational angle, left or right breast, patient position, etc. are also displayed (not shown in FIG. 12B).

Figure 12C:
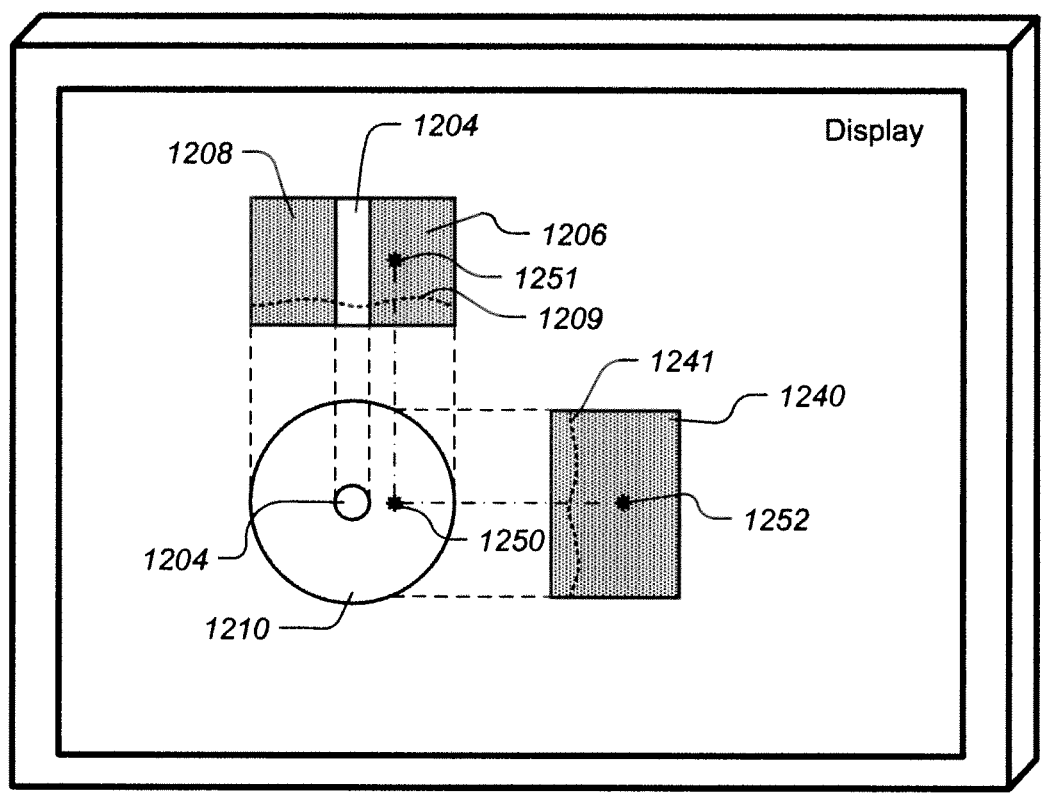
FIG. 12C illustrates a display of a coronal slice with an abnormality and of associated orthogonal views that contain the abnormality.

An abnormality may be noted in a displayed coronal thick-slice of the patient's breast. As illustrated in FIG. 12C, when an abnormality 1250 in the coronal slice is found, with a click on the abnormality 1250 with a mouse or controller or by some other input, corresponding abnormality 1251 in the original 2D radial scan thin-slice image or images containing this abnormality can then be automatically pulled up and displayed through suitable algorithms programmed in frame 104 as known in ultrasound image processing technology. Similarly, a constructed 2D image 1240, orthogonal to view 1208, containing this abnormality 1252 can also be shown simultaneously. Also visible in constructed image 1240 is chestwall 1241.

FIG. 13A illustrates the use of an ultrasound transducer 1314 that has a concavely curved bottom 1314A facing and compressing and scanning a patient's breast 1304 that is compressed with a rotating, concavely shaped template 1312 having a central opening through which the nipple 1305 protrudes. While template 1312 is illustrated as compoundly concavely curved, it can be planar or spherical in shape, and transducer 1314 can still have a similar concavely curved lower side 1314A, or it can have a generally planar lower side. In embodiments where several transducers concurrently scan a breast, e.g., as in FIG. 10, each transducer can have a concave lower side or some of the transducers (e.g., the shortest transducer(s)) can have straight lower sides, or all can have straight lower sides. In cases where the template 1312 is concave such as shown in FIG. 13A, the departure angle $\phi$ can be greater than 2.5°, but preferably would not exceed about 20° as shown. FIG. 13B illustrates a side view of transducer 1314 having a curved lower side 1314A in a radial plane, but a straight lateral lower side. FIG. 13C illustrates a side view of a multi-array transducer 1314C, according to some embodiments. The multi-array transducer 1314C is wider as shown. Additionally, the lower curved side 1314d can be concavely curved both in the radial and in the lateral dimensions to match a concavely curved template 1312.

Figure 14:
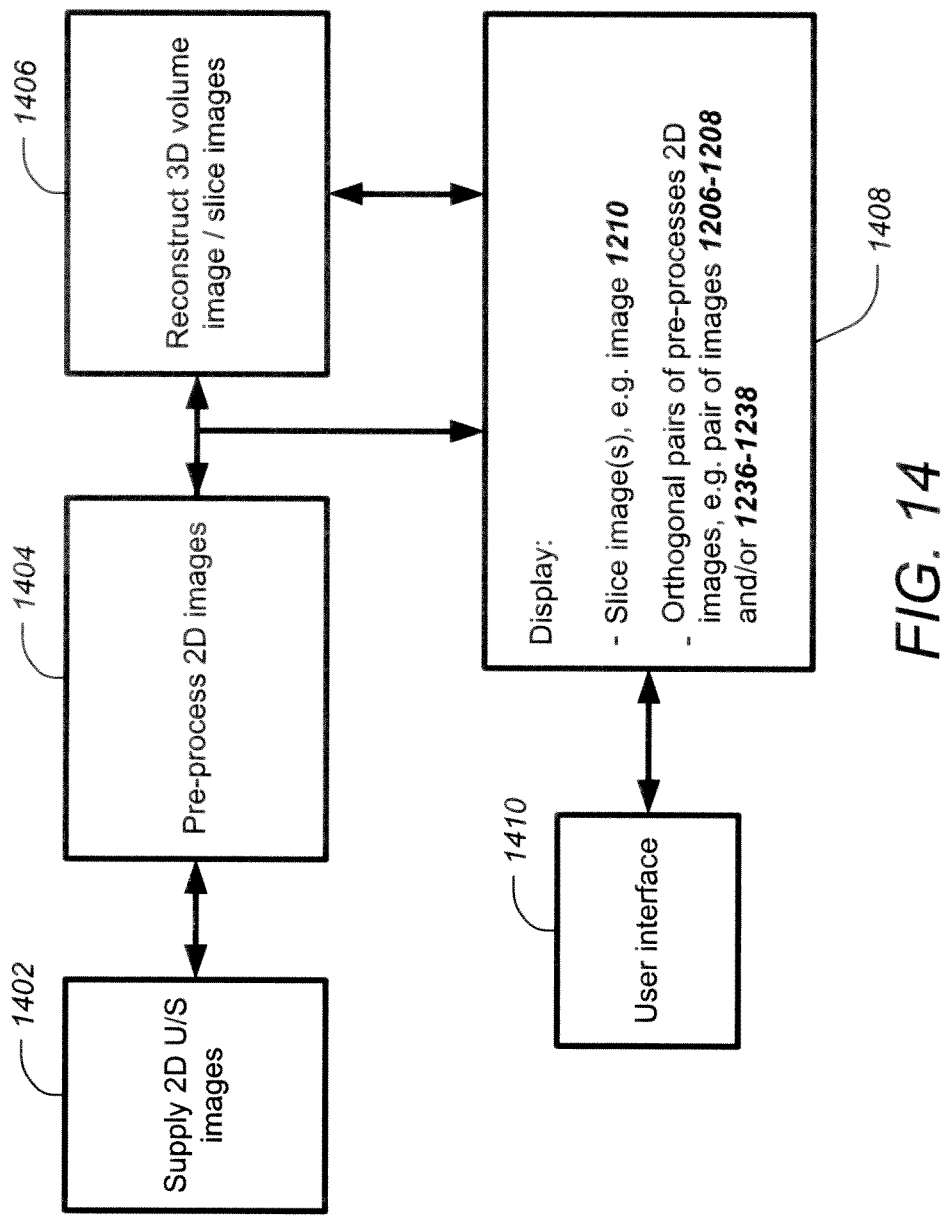
FIG. 14 illustrates in block diagram form a system for acquiring and processing ultrasound images and displaying resulting processed images in cooperation with a user interface.

FIG. 14 illustrates in block-diagram form certain computer-implemented facilities for carrying out scanning and image processing and display according to embodiments described above. One or more ultrasound transducers 1402 scanning the breast as described above supply raw 2D ultrasound images to a pre-processing facility 1404 that applies various algorithms to the raw images as known in the pertinent technology to generate pre-processed 2D thin-slice images each representing a planar section of the breast conforming to a plane extending in the chestward direction (transverse to the coronal plane). These pre-processed 2D images are supplied to a facility 1406 that reconstructs from them a 3D structure of voxel values of the breast and, if the 3D image is in a form different from a stack of coronal slice images representing breast slices of selected thicknesses (e.g., as a non-limiting example, slices that are 0.5-10 mm thick) the facility generates such slice images from the 3D image of the breast. Thus far, the operation is similar to the known generation of 2D and 3D images and slice images in commercially available FFBU devices, except that the raw 2D thin-slice can all be original scan images rather than thin-slice images reconstructed from the 3D representation of voxel values, which reconstructed images may not be as true as the actual original scan image. A display facility 1408 receives the pre-processed 2D images from facility 1404 and the 3D image and/or the coronal slice images from reconstruction facility 1406. The display facility 1408 includes one or more computer display screens and computerized processing circuits and software, and operates under the control of a user interface 1410 to generate and display slice images such as 1110 through 1120 as illustrated in FIGS. 11A and 11B and/or a slice image such as 1210 together with pairs of pre-processed 2D images such as 1206-1208 and 1236-1238 illustrated in FIGS. 12A and 12B. The coronal slice images of FIG. 11B can be displayed concurrently or in sequence or in a cine mode. Per operator control through interface 1410, the images can be moved on the display screen or superimposed or one or more can be changed, such as by changing the orientation of the slice that the image represents, or the thickness of the slice, or the transparency of one or more superimposed images, or the type of projection that generated the slice (e.g., minimum or maximum intensity projection) by applying image processing techniques known in the ultrasound imaging field and/or in other image processing and display fields such as post-production of still or video images. Similarly, the images illustrated in FIG. 12B can be displayed in the illustrated format or in other formats known in the pertinent technology. As non-limiting examples, the slice image 1210 of FIG. 12B can be changed to represent a slice that has a different orientation or thickness or to an image of the slice that was generated in a different way (e.g., by a different type of projection), and the 2D images or FIG. 12B also can be varied under control of inputs from interface 1410, such as by rotating their planes around an axis normal or only transverse to the coronal plane, by changing the angle between the planes of the two pairs of the 2D images, by changing the range of pixel values in the images (i.e., by controlling the window width of the images), and in other ways known in the technology of displaying pixel value images. Some or all of the facilities illustrated in FIG. 14 can be implemented by programming the computing equipment in frame 104 or FIG. 1A, or by carrying out processing in separate computer equipment connected thereto, or in a workstation that is remote from frame 104 but is coupled therewith to receive the 2D images that the transducer(s) generate. The software controlling the operation of the equipment illustrated in FIGS. 1A and 14 can be stored in non-transitory form in computer-readable media to form a program product.

According to some embodiments, images from prior examinations can be shown together with images of the current examination of a patient using display facility 1408 to view changes over time. According to some embodiments, an image that represents differences over time between the images is displayed using display facility 1408. According to yet other embodiments, CAD (computer aided detection) results and/or other image enhancing results can also be displayed using display facility 1408.

Figure 14A:
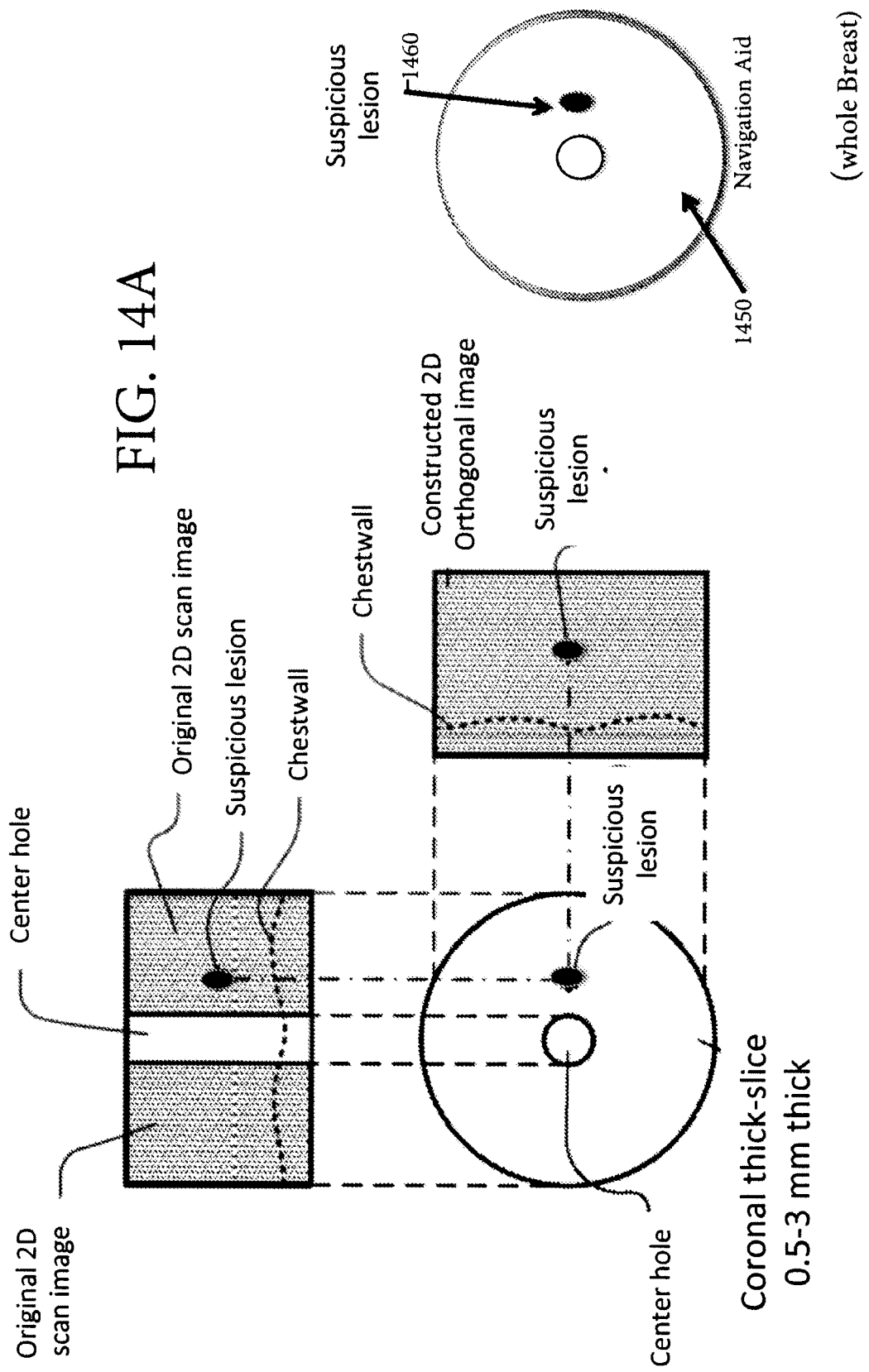
FIG. 14A illustrates a display of images derived from a rotary scan of a breast with equipment such as illustrated in FIG. 1A, including an enhanced whole-breast navigator aid with an abnormality found therein, and three other images that contain the same abnormality—an original thin-slice chestwardly oriented image, a constructed thin-slice image orthogonal thereto, and a coronal thick-slice image.

FIG. 14A illustrates an example of a display resulting from a rotary scan of a breast and processing of the resulting measurements as described in the several examples of such processing in this patent specification, and includes at lower right a whole-breast navigator or guide image or aid 1450 that highlights and enhances a representation of a suspicious lesion indicative of a likely abnormality. The display includes at lower left an image of a coronal thick-slice that for example can be in the indicated range of thickness, and includes above and to the right of the coronal slice image two thin-slice images. For example, one of the thin slice images can be an original 2D scan image and the other can be a constructed thin-slice image of breast anatomy in a plane orthogonal to that of the original thin-slice image. The coronal thick-slice image and each of the thin-slice images can be automatically selected to include the abnormality, for example in response to a user pointing to the abnormality in the whole-breast navigator or guide image or aid or in response to some other action or event.

In one example, a display such as in FIG. 14A includes only the original scan thin-slice image shown concurrently with the whole-breast navigator aid and the thick-slice coronal image, without the constructed 2D orthogonal image seen in FIG. 14A. Preferably, the thin-slice image is an original 2D image derived from scanning the breast with an ultrasound transducer. As noted, the thin-slice original image and the thick-slice constructed coronal image are automatically selected, based on the 3D structure of voxels of the breast and the enhanced navigator aid to contain an abnormality that a used points to in the navigator image, for example by hovering a pointer over the abnormality in the navigator aid. If the whole-breast navigator aid contains only a single abnormality, the pop-ups can appear without prompting by the user. Or, a protocol can be included in the system to automatically produce relevant pop-ups for an abnormality next to one that the user has just viewed and considered, with or without prompting by the user.

Skilled persons would appreciate that any of a variety of different frame assemblies can be used that position, compress against the breast, rotate, and otherwise manipulate the scanning template, whether the scanning template is permanently used and re-used for different patients or is disposable for each patient, without departing from the scope of the present teachings. Moreover, in one or more alternative preferred embodiments, the basic profile of the radial scanning template can be elliptically shaped, etc., rather than strictly circular-shaped as indicated in some of the attached drawings. The scanning surface of the ultrasound transducer can be arched or otherwise made to conform to another curved surface in a similar manner, if desired. Therefore, references to the details of the embodiments are not intended to limit their scope.

Figure 15:
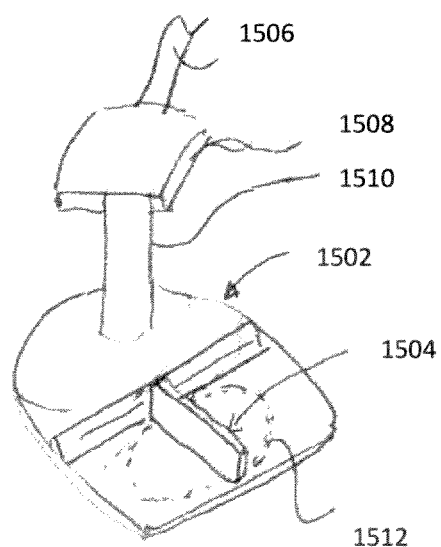
FIG. 15 illustrates in perspective a scanning mechanism that uses linear scanning motion rather than the rotary scanning motion of the FIG. 1A equipment but is otherwise similarly used as a part of an overall breast ultrasound system.

FIG. 15 illustrates a scanning pod 1502 that scans a chestwardly compressed breast with an ultrasound transducer 1504 in a generally linear pattern rather that in a rotary pattern as in FIG. 1A, and produces chestwardly oriented 2D original slice images from which a 3D structure of breast voxel values can be constructed. The scanning pod 1502 can be attached to an articulated arm 1506 similar to arm 106 of FIG. 1, and can be associated in a similar manner with a processor frame such as frame 104 of FIG. 1. Pod 1502 can be similar or even the same as used in a commercially available system currently offered commercially in the U.S.

by GE Healthcare under the trade name ABUS and previously available from U-Systems, Inc. of California. Such a system is discussed in U.S. Pat. Nos. 7,828,733 and 8,496,586. As in the commercially available system, scanning pod 1502 can be brought down to chestwardly compress an upwardly facing breast of a patient 102 resting on a table in a position such as the supine position. Pod 1502 includes transducer 1504 that is driven mechanically, electromechanically or otherwise to scan the compressed breast through a coupling medium and send ultrasound energy into the breast and receive a sonographic response while compressing the breast portion that it contacts through the coupling medium. A computer-driven scan control mechanism 1508 drives the transducer or at least controls some aspects of the scanning movement, through a linkage mechanism 1510. Transducer 1502 scans a compressed breast schematically indicated at 1512 in a single sweep or swath or more typically in several partly overlapping swaths as is known in the commercial system, through a coupling medium such as a gel-wetted fabric between the bottom surface of pod 1502 and the breast.

Figure 16:
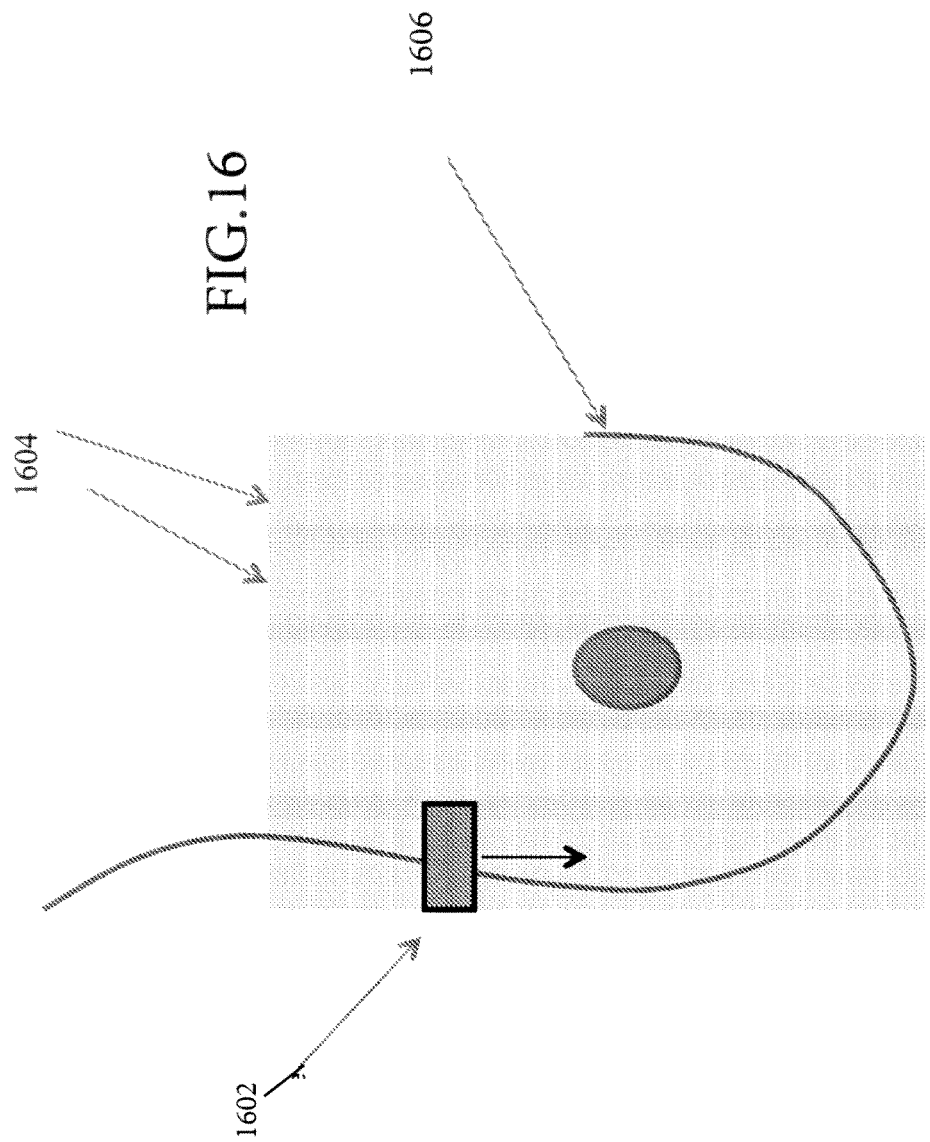
FIG. 16 illustrates an ultrasound transducer scanning a breast linearly along successive overlapping sweeps.

FIG. 16 illustrates yet another way to obtain chestwardly oriented 2D original slice images. An ultrasound transducer 1602 scans a chestwardly compressed breast 1606 along a succession of partly overlapping sweeps, swaths, or scan rows 1604 that are generally linear to thereby cover the entire breast. The 2D images from the respective swaths can be stitched into a 3D structure representing the breast, with appropriate blending of the overlapping portions. Transducer 1602 is supported by a linkage (not shown) similar to linkage 118 of FIG. 1A and linkage 1510 of FIG. 15 and can be driven by a device similar to computer-driven scan controllers 118 of FIG. 1A and 1508 of FIG. 15 but configured to drive the transduced along swaths 1604. The scanning arrangement can be similar to or even the same as that used in an ultrasound breast scanning system offered by Sono-Cine of Reno, NV under the trade name AWBUS. The system includes a known ultrasound processing engine (not shown) to produce images for display from the sonographic response collected by transducer 1602.

Figure 17:
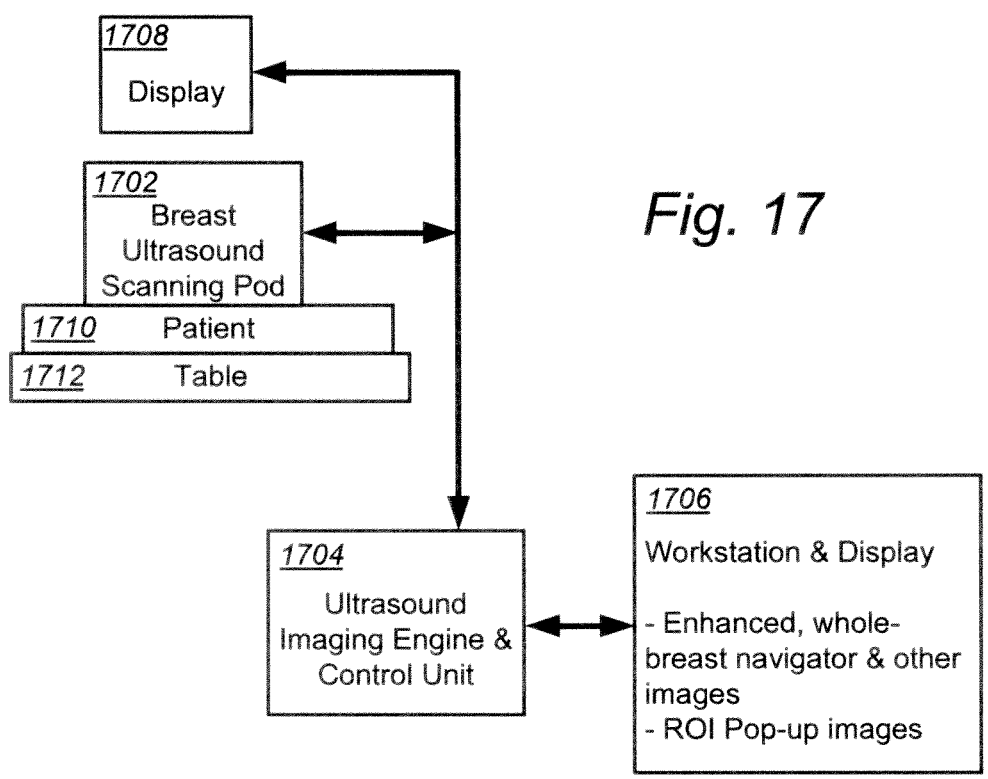
FIG. 17 illustrates in block diagram form major portions of a breast scanning system.

FIG. 17 illustrates in block diagram form an overall arrangement of equipment that can use the rotary scan of FIG. 1A, the generally linear scan of FIG. 15, and/or the narrower swaths scan of FIG. 16, or alternative scanning patterns. Scanning pod 1702 and control unit 1704, which include an ultrasound transducer and any needed computer-driven scan controller mechanism and linkage mechanism, cooperate to scan a chestwardly compressed breast and produce a sonographic response that typically is in the form of 2D chestwardly oriented thin-slice images. Control unit 1704 uses the 2D thin-slice images to produce a 3D structure of the scanned tissue voxel values. Further operations in control unit 1704 and/or in workstation 1706 produce thick-slice images of the sonographic response that typically conform to coronal planes but if desired can conform to other planes or even to curved surfaces, and enhanced whole-breast navigator aids and region of interest (ROI) images that can be displayed at workstation 1706 and/or at a display 1708 that can be on a common support with pod 1702. Patient 1710 is on a table 1712, generally in a supine position but can be in other positions so long as the breast being examined faces generally up and is compressed by pod 1702 generally chestwardly down. The connection between control unit 1704 and workstation 1706 can be wired or wireless, directly or indirectly such as through a hospital's PACS facilities. According to some embodiments, information can be accessed from a server via a standard protocol such as DICOM. Further details of the basic system can be found in the cited patents or in information regarding the commercially available system but are not included here for the sake of conciseness. The system is modified to process the sonography response as described below, using the computing facilities of engine 106 and/or workstation 110 through the operation of algorithmic software, firmware, and/or hardware to carry out processing described below.

Figure 18:
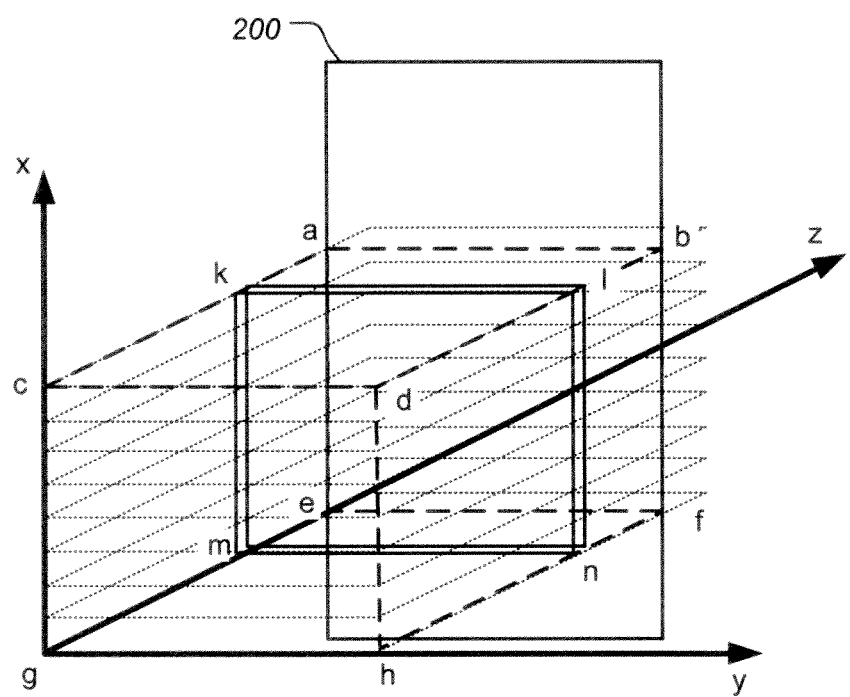
FIG. 18 illustrates a 3D structure of voxels of a breast, a coronal thick-slice in the structure, and chestwardly directed planes of thin-slices of the breast.

FIG. 18 illustrates aspects of chestward compression scan orientations in relationship to a 2D coronal thick-slice of a patient's breast, as well as a volume from which an enhanced, whole-breast navigator overview image can be produced, according to some embodiments. Shown are a 2D coronal thick-slice guide (k,l,m,n), and the volume (a,b,c,d, e,f,g,h) from which the enhanced, whole-breast navigator overview image can be produced. Chestwall 200 is also shown. The planes a,b,c,d to e,f,g,h are original axial thin-slice scanned images. The z-direction in FIG. 18 is a chestward direction, and the axial images are in planes that are perpendicular to the length of the patient.

In this patent specification, the original chestwardly oriented scan images are referred to as thin-slice images because each represents a very thin slice of tissue, such as 0.1 mm or even less. The term thick-slice image refers to an image that typically represents a tissue slice that is 0.5-20 mm thick, although variations are possible. The term whole-breast navigator overview image or aid refers to an image that represents a 3D volume of tissue that typically is the entire volume of interest that generates the sonographic response, such as all the scanned breast tissue after segmenting out tissue that is not of interest such as ribs and muscle, or represents at least tissue of much greater thickness than a thick-slice. The sonographic response content that is segmented out typically includes responses from tissue such as the patient's ribs, chest wall (pectoral muscle (s) and connective tissue), and/or skin plus possibly a layer of breast tissue close to the skin. The term user in this patent specification refers to the person who operates the system to generate the sonographic response from which the images are derived and/or a person who views or otherwise utilizes the images to screen and/or diagnose a breast or a patient.

In overview, in the disclosed embodiments one or more ultrasound transducers transmit ultrasound energy into a patient's breast and receive sonographic responses that are converted through processing in computer circuits into a three-dimensional (3D) structure representing tissue producing the responses, which 3D structure thereafter is enhanced by removing influences of non-breast tissue that is not of interest. The so-enhanced 3D structure is acted on to produce one or more enhanced, whole-breast navigator overview images or aids and pop-ups that are uniquely configured to speed up the screening and diagnosis of the patient's breast and to reduce occurrences of missed lesions. The navigator overview images or aids can be further configured to include indications, such as computer-aided detection (CAD) marks or enhancements that rely mainly on other processes and can identify as such both likely malignant and likely benign abnormalities found in the breast and enhance the representation of certain aspects of abnormalities, and can be displayed together with other images that can help further characterize the abnormalities.

Figure 19:
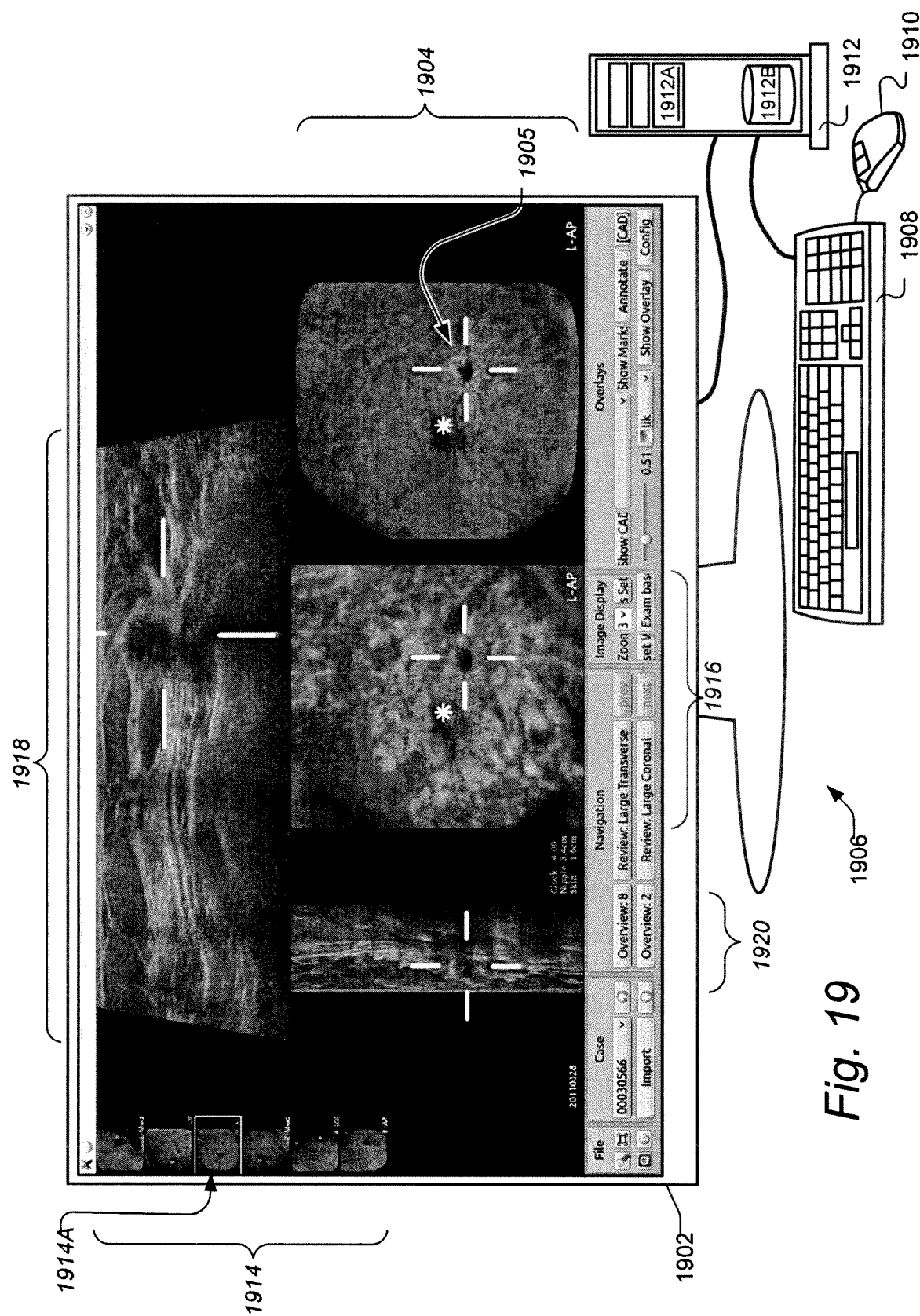
FIG. 19 illustrates an overall system for ultrasound breast studies, including an example of a display showing a whole-breast navigator aid with an enhanced representation of an abnormality, several reduced-size images of scans of the breast, and several slice images each containing the abnormality that can be shown as pop-ups, namely, a thick-slice coronal image, a thin-slice chestwardsly oriented original scan image, and a constructed thin-slice orthogonal image.

FIG. 19 illustrates examples of images produced and displayed in accordance with disclosed embodiments. A computer screen 1902 displays an interactive user interface including on the right a 2D representation of a 3D enhanced, whole-breast navigator overview image or aid 1904 that includes a representation of an abnormality 1905. Image 1904 is graphically altered to provide improved navigation pertaining to the characteristics of the lesion features to the user/physician as to which lesion(s) can or should be given priority for interpretation. For example, it can be marked to identify the abnormality 1905 as benign or malignant. Display screen 1902 in this example further includes at upper left reduced size and resolution versions 1914 of all or at least several of the whole-breast navigator overview images of the individual 3D scans of both breasts of the patient. In this example, three 3D volumetric scans are made on each breast of the patient. The reduced resolution version 1914 includes the currently viewed image 1914A is displayed in higher resolution and larger size as enhanced, whole-breast navigator overview image 1904. A spiculated lesion 1905, which has a high probability of being a cancer, is shown in a coronal thick-slice view 1916 that can be automatically selected to include the abnormality 1905 seen in the navigator aid 1904. Corresponding views in the original 2D original thin-slice scan image 1918 and a constructed orthogonal 2D thin-slice image 1920 also can be automatically selected to show the same abnormality 1905, which in this case exhibits characteristics of high probability of being a cancer. This automatic selection can be in response to a user pointing to lesion 1905, for example with a user interface device, or even without pointing if there is only one abnormality shown in navigator aid 1904. The whole-breast navigator image 1904 can be altered such that the spicules of the spiculated lesion 1905 can be seen prominently therein. This added information allows the user/physician to pay immediate attention to this feature.

The display of FIG. 19 can be set to show various protocols. One preferred example is a set of the 2D representation of the enhanced 3D navigator image, a 2D representation of a constructed thick-slice coronal image that includes a representation of a selected abnormality seen in the navigator aid, and an original 2D thin-slice image that includes the same abnormality and possibly the reduced-size images seen at upper left (but without the constructed orthogonal thin-slice image). Another protocol may put on the display the same or similar set of images of both breasts of a patient, or images from studies of the same breast or breasts taken at different times. The display is interactive so that a user can scroll through thin-slice images adjacent in space to the one that automatically pops us when a user points to an abnormality in the navigator aid, and through thick-slice images adjacent to the automatically displayed version.

In FIG. 19, a user interface/workstation 1906 includes display 1902, input devices such as keyboard 1908 and mouse 1910, and a processing system 1912. Other user input methods such as touch sensitive screens can be used. User interface/workstation 1902 can be unit 104 of FIG. 1A, or units 1404 and 1406 of FIGS. 14, or 1704 and 1706 of FIG. 17. Processing system 1912 can be a suitable personal computer or a workstation that includes one or more processing units or modules 1912A, input/output devices such as CD and/or DVD drives, internal storage 1912B such as RAM, PROM, EPROM, and magnetic tape storage media such as one or more hard disks for storing the medical images and related databases and other information, as well as graphics processors suitable to power the graphics being displayed on display 1902.

In one example, processing system 1912 comprises a first programmed computer processor module coupled with the ultrasound transducer of FIG. 1A, 15 or 16 to receive the ultrasound responses therefrom and configured to apply computer processing thereto producing a three-dimensional (3D) structure representing sonographic response characteristics of volume elements (voxels) of scanned tissue, a second programmed computer module configured segment out influences of scanned tissue that is not of interest and to apply computer processing to the resulting 3D structure to find therein tissue abnormalities, a third programmed computer module configured to produce enhancements of at least some of the found tissue abnormalities, a fourth programmed computer module configured to produce a navigator aid structure depicting the entire scanned breast tissue of interest and the abnormalities therein that have been enhanced by the third programmed computer module, and a computer display configured to produce and display a depiction of the navigator structure with the abnormalities therein enhanced by the fourth programmed computer module and to respond to user input regarding an abnormality in the navigator structure by producing and concurrently displaying pop-up depictions of the abnormality as it appears in a coronal slice of the scanned tissue that has a selected thickness and in one or more thin-slice images that conform to chestwardly directed planes.

In contrast to using a coronal thick-slice image as a "guide image" as in conventional approaches, the user interface/workstation 1912 produces and uses a whole-breast navigator overview image 1904 that combines information from the whole 3-D structure of breast tissue of interest. Also in contrast to conventional thick-slice or even possible entire-breast images, the entire-breast navigator overview images described in this patent specification are enhanced by segmenting out influences of non-breast tissue that can hide or obscure important abnormalities, and can include enhanced depictions of abnormalities to highlight or suppress features thereof and to highlight specified abnormalities and characteristics thereof.

Figure 20:
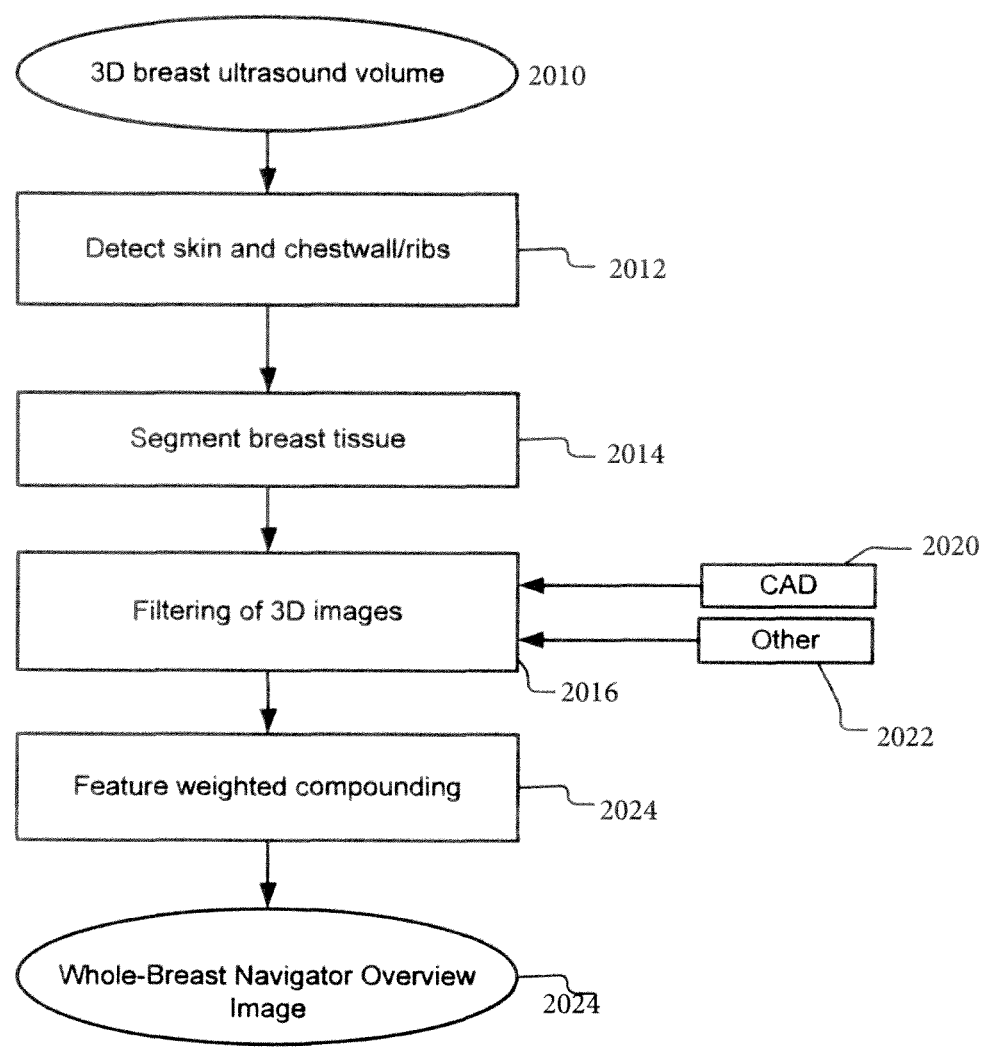
FIG. 20 illustrates computer modules involved in obtaining ultrasound measurements of a breast and producing and using other breast representations, including a whole-breast navigator aid.

FIG. 20 is a flow chart illustrating aspects of one example of producing and displaying an enhanced, whole-breast navigator overview image. In step 2010, a first programmed computer module constructs a 3D structure of a breast, for example by carrying a rotary or a linear scan of a breast as described above and constructing the 3D structure from the chestwardly oriented thin-slice images of sonographic response. Typically, Cartesian coordinates are used in processing the scan measurements and constructing the thin-slice and thick-slice images, the 3D structures of voxel values, and the enhanced navigator image. In rotary scanning as illustrated in FIG. 1A, the position of a point on the ultrasound transducer can be tracked in terms of its distance R from the center of rotation and the current angle a (alpha) from a starting angle. The conversion to Cartesian coordinates is well known—the x-coordinate of the point and the column of breast voxels under the point is x=$R\cos\alpha$ and y=$R\sin\alpha$. In this manner, the illustrated computer modules can convert the rotary coordinates R,$\alpha$ to the required Cartesian coordinates for further processing. In step 1214, a second programmed computer module segments breast tissue, for example by removing influence of ribs and/or other non-breast tissue and skin and possibly a layer close to the skin, and in step 2016 filters the resulting breast 3D structure, for example by computer-aided detection algorithms and/or other computer-processing operations, to find and possibly characterize suspected abnormalities. The skin region and a layer underneath can be simply defined as the region within a certain distance range from the top or from the scanning ultrasound transducer, say 0 to 2 mm. The filters applied in step 2016 can be a gradient conversion filter configured to enhance dark rounded shapes that resemble masses in the breast and a line conversion filter configured to enhance lines radiating from a center that resemble a spiculation or architectural distortion in the breast. The filters can include a computer aided detection (CAD) algorithm 2020 that detects and ranks the lesions by likelihood of being actual lesions and/or by likelihood of malignancy. Other filters 2022 can be derived from techniques such as minimum voxel value, Doppler data, and/or elastography data. In step 2018, a third programmed computer module applies computer processing to the results of step 2016 to enhance at least some of the found abnormalities, for example by feature weighted compounding. According to some embodiments, weights, w(x,y,z) for compounding are generated by combining the outputs of the filters:

$$w(x,y,z) = \Sigma_i^N k_i f_i(x,y,z)$$

where N is the total number of filters, $f_i(x,y,z)$ is the output of i-th filter and $k_i$ is a constant scaling factor for i-th filter. The weight is also normalized from 0 to 1 as the probability of a voxel overlap with a malignant lesion.

In step 2024, a fourth programmed computer module constructs and displays an enhanced, whole-breast navigator overview image a(x,y) by projecting the 3D structure produced in step 2018 along the z direction (preferably excluding some or all of skin and underlying thin layer, chestwall and rib regions) modulated by the weight. The relationship below is one example of the projection by taking the minimum value of the weighted intensity alone the z-axis.

$$a(x, y) = \text{MIN}_{across\ z}(I(x, y, z)(1-w(x, y, z)))$$

where I(x,y,z) is the intensity or voxel value of the 3D ultrasound structure.

Figure 21A:
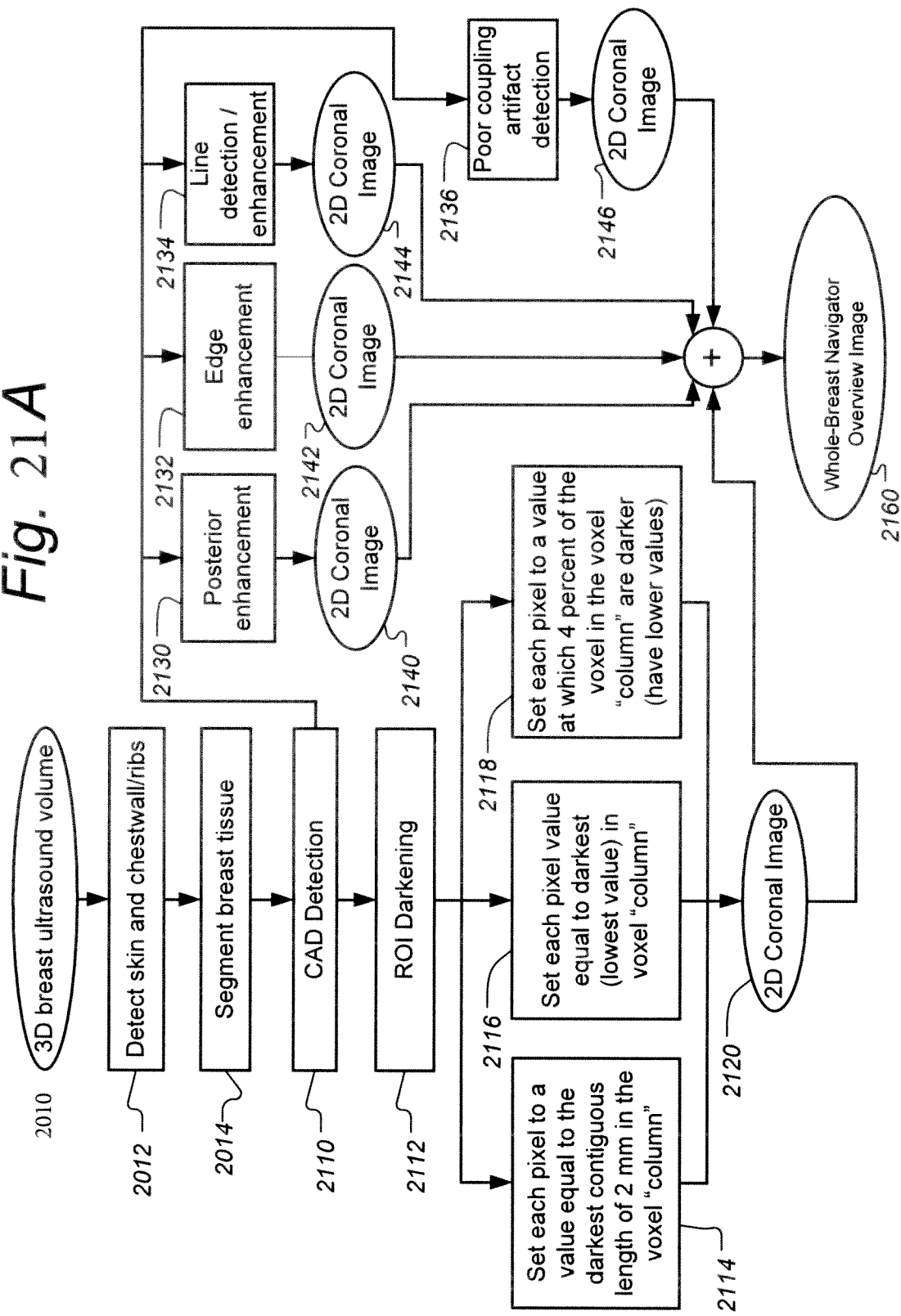
FIG. 21A illustrates an example of equipment and methods of producing a whole-breast navigator aid and related pop-ups.

FIG. 21A illustrates in more detail certain aspects of producing an enhanced, whole-breast navigator overview image based on a 3-D structure of a breast using CAD, according to some embodiments. Blocks 2010, 2012, and 2014 represent programmed computer modules similar or identical to those shown and described with respect to FIG. 20. In block 2110, a programed computer module applies CAD algorithms to find regions of interest (ROIs) containing likely abnormalities. For diagnostic procedures, users/physicians have been using 2D ultrasound to distinguish and classify breast lesions. For example, see the study by Stavros et al. in 1995 Radiology, Vol. 196, pages 123-134, entitled: "Solid breast nodules: Use of sonography to distinguish between benign and malignant lesions". CAD algorithms have been developed to distinguish between benign and malignant lesions in 2D and 3D images. For example, see (a) the study by Drukker et al. in 2002 Medical Physics, Vol. 29, pages 1438-1446, entitled: "Computerized lesion detection on breast ultrasound"; and (b) the study by Tan et al. in 2012 IEEE Trans. on Med. Imaging, Vol. 31, pages 1034-1042, entitled: "Computer-aided lesion diagnosis in automated 3D breast ultrasound using coronal spiculation". For screening purposes, most, if not all, of the prior CAD developments have been concentrated on detecting malignant lesions. However, according to some embodiments in block 2110, a CAD algorithm can be used to detect likely malignant lesions as well as likely benign lesions. A primary reason for detecting benign lesions and marking them in 3D volumetric ultrasound is to lower the distraction by these likely benign lesions during the interpretation by users/physicians in screening procedures. For further examples of CAD and computer-aided classification, see, e.g. Karen Drukker, et. al., "Computerized Detection Of Breast Cancer On Automated Breast Ultrasound Imaging Of Women With Dense Breasts," Med. Phys. 41 (1), pp. 012901-1-9, January 2014; Tao Tan, et. al., "Computer-aided Detection of Cancer in Automated 3D Breast Ultrasound," IEEE Transactions On Medical Imaging, Vol. 32, No. 9, September 2013, pp. 1698-1706; Tao Tan, et. al., "Computer-Aided Lesion Diagnosis in Automated 3-D Breast Ultrasound Using Coronal Spiculation," IEEE Transactions On Medical Imaging, Vol. 31, No. 5, pp. 1034-1042, MAY 2012; and Woo Kyung Moon, et. al., "Computer-Aided Classification Of Breast Masses Using Speckle Features Of Automated Breast Ultrasound Images," Med. Phys. 39 (10), pp. 6465-6473, October 2012. One of more of the CAD algorithms in the cited publications can be used in step 2110, by suitably configuring ultrasound engine 104, 1406, 1704, 1706, and/or 1812 by software, firmware, and/or hardware, as can be appreciated by persons skilled in the technology.

Following CAD detection of ROIs in block 2110, according to some embodiments the ROIs are darkened in block 2112, for example by scaling each voxel value within each ROI according to the likelihood of malignancy as determined by the CAD process in block 2110. In one example, all voxels within an ROI having a 70% chance of malignancy as determined by the CAD algorithm, are multiplied by 0.3 (where 1=likelihood of malignancy) which will darken the pertinent voxel values in the ROI. According to other embodiments, other methods of ROI-weighted voxel darkening can be used.

According to other examples, in block 2112, the ultrasound 3D structure of voxel values is split into low and high frequency components, and a volume structure is produced that is a weighted combination of the low-pass (background) and high-pass (signal) components. According to some embodiments, this is accomplished by producing a background volume with any of a number of known techniques (including nonlinear smoothing, in which case the background image isn't strictly "low-pass" in the traditional sense) and deriving the signal volume as the difference between the original and the background. The simple summation of these derived background and signal volumes can reproduce the original 3D structure faithfully. Over most of the 3D volume, the two components are summed with equal weight, i.e., in a simple summation, but in the neighborhood of a CAD-found ROI of a likely abnormality, the signal component is weighted more heavily, emphasizing image detail in that volume.

After each CAD-found ROI is darkened in block 2112, a suitable method is used to select the appropriate pixel values for a 2-D representation of the 3D navigator aid structure, such that the user's attention can be drawn to the appropriate features from the 3-D image data.

According to some embodiments, one or more graphical alteration techniques are used to further enhance the usability of the resulting navigator aid. Examples of such techniques include posterior enhancement 2130, edge enhancement 2132, line detection/enhancement 2134, and poor coupling artifact detection 2136. The techniques applied in computer modules 2130, 2132, 1734, and 2136 generate new 2D images 1740, 1742, 1744, and 2146 respectively. Posterior enhancement block 2130, according to some embodiments, adds pixel values from an area below a detected ROI, which tends to make malignant lesions darker in the center, but make benign cysts lighter in the center. In block 2132, according to some embodiments, a high pass filter is used to enhance edges of ROIs. In some examples, the negative values of voxels of pixels are clipped to zero and then the filtered results are added back to the image. In block 2134, according to some embodiments, a line detection/enhancement technique is carried out in a volume of voxels including and above a detected lesion. Techniques 2130, 2132, and 2134 are described in further detail in FIGS. 23A, 23B, 24A and 24B, infra. In block 2136, a technique is used to detect artifacts resulting from locally poor acoustic coupling. Some or all of the individual 2-D coronal images 2120, 1721, 2142, 2144, and 2146 are summed together at 2150. According to some embodiments, equal weighting can be used, but it has been found that in many cases a varying weighting algorithm can be more effective in generating a highly useable enhanced, whole-breast navigator overview image. In many cases it has been found that the 2-D coronal image 2120 is more heavily weighted, although the individual weights depends on which projection method (e.g. 2114, 2116, or 2118) and what types of graphical detection/enhancement techniques (e.g. 2130, 2132, 2134, and 2136) are used. The 2D coronal images 2120, 2140, 2142, 2144, and 2146 can be intermediate versions of the enhanced, whole-breast navigator overview image. Alternatively, they can be successive thick-slice images that are combined at 2160 into an enhanced, whole-breast navigator overview image.

Figure 21B:
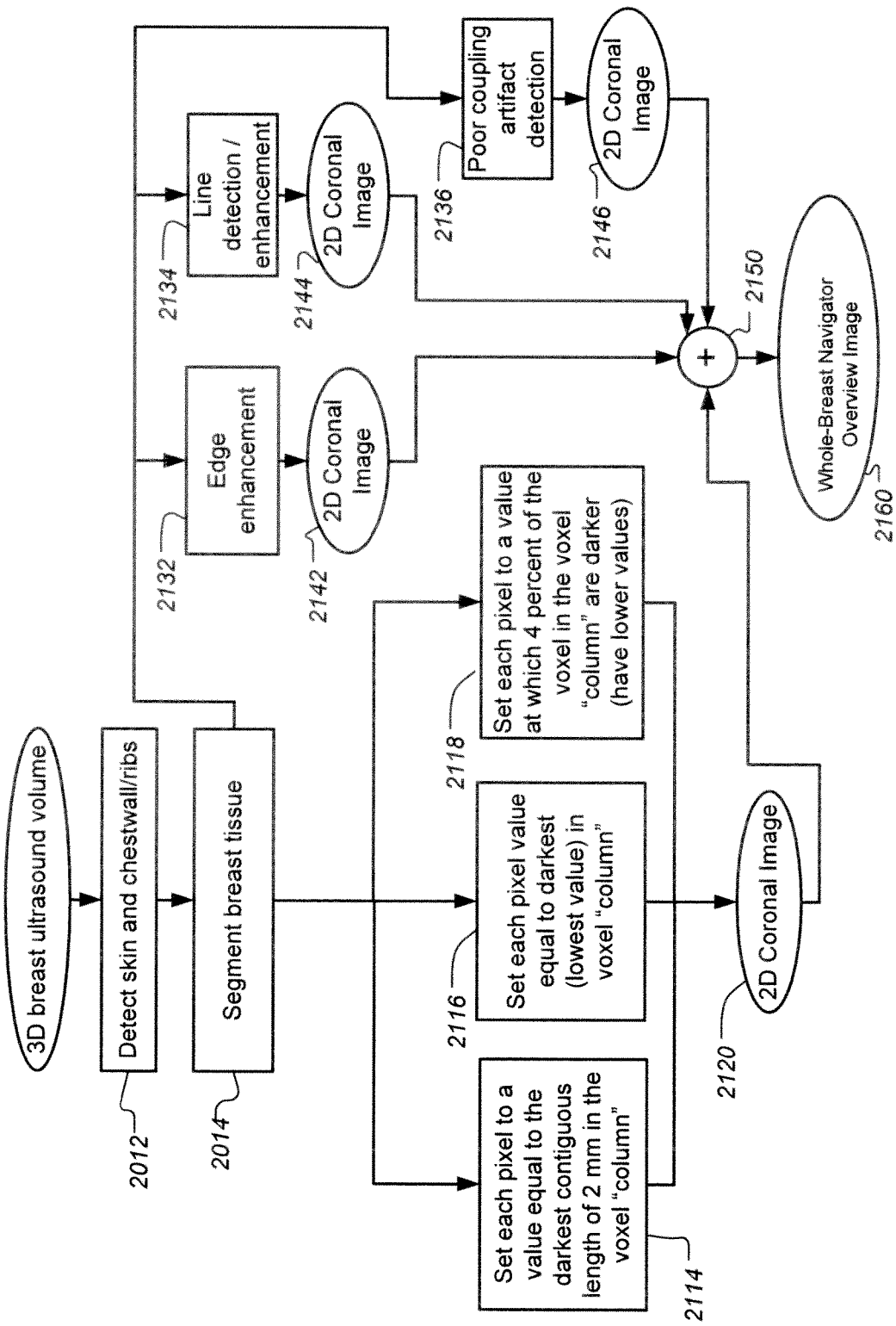
FIG. 21B illustrates another example of such equipment and methods.

FIG. 21B illustrates aspects of producing an enhanced, whole-breast navigator overview image based on 3-D image data without using CAD, according to some embodiments. FIG. 21B is similar or identical to FIG. 21A in many respects so comparable equipment is similarly numbered, but can be used to produce a suitable enhanced, whole-breast navigator overview image 2160 without the use of a CAD algorithm. In FIG. 21B, the skin, chest wall, and ribs are detected and segmented in blocks 2012 and 2114. One of the projection techniques 2114, 2116, or 2118 is then used to generate image 2120. According to some embodiments, image 2120 may be suitable for use as an enhanced, whole-breast navigator overview image 2160 without further alteration. According to some other embodiments, edge enhancement and line detection/enhancement algorithms 2130 and 2134 can be applied to the entire segmented 3-D image (rather than just to selected volumes based on a CAD-found ROIs). According to some embodiments, the coupling artifact detection technique 2136 can be used. The resulting 2-D images are then summed together at 2150 using suitable weighting to generate the final enhanced, whole-breast navigator overview image 2160. As in the process of FIG. 21A, an alternative is to process several thick-slice images in the indicated manner and then combine then into the desired enhanced, whole-breast navigator overview image in step 2160.

Figure 22:
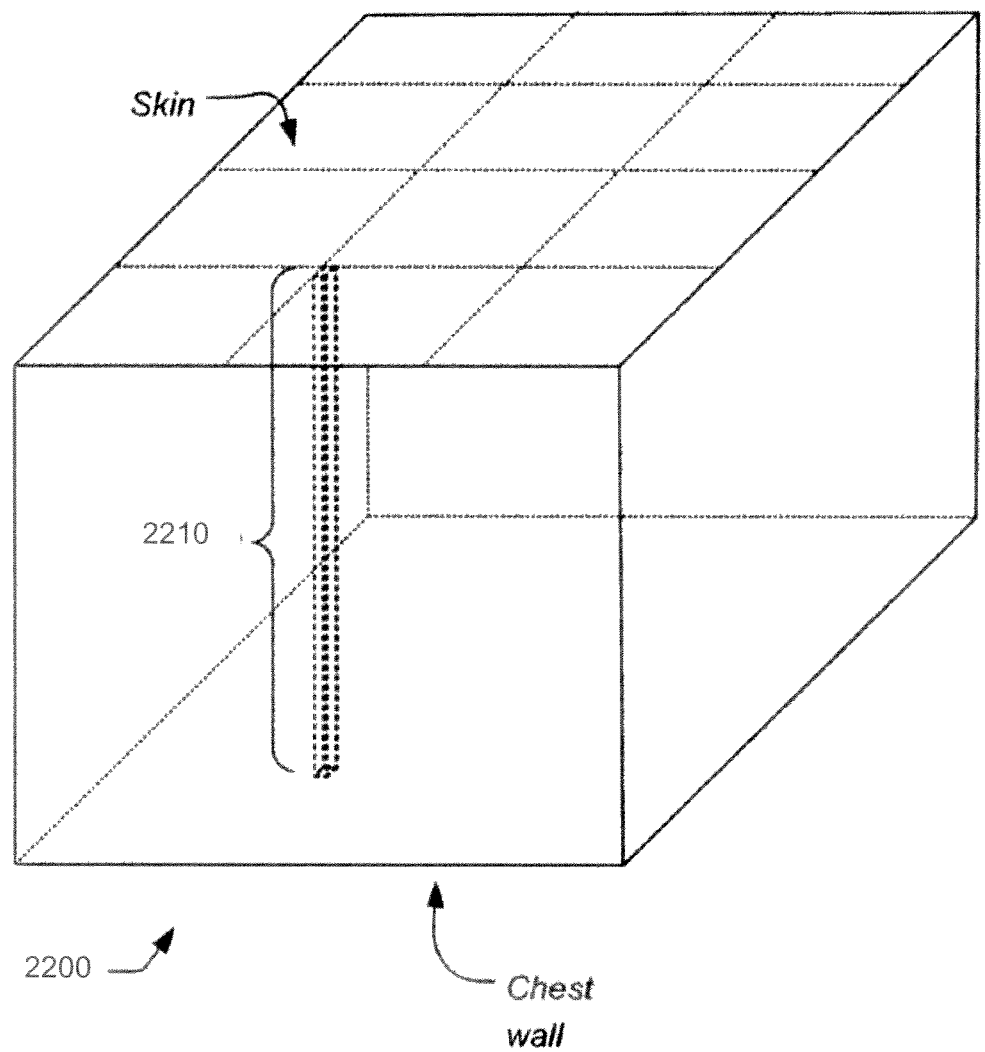
FIG. 22 illustrates a geometry related to producing a 2D representation of a 3D whole-breast navigator aid.

FIG. 22 is a diagram illustrating aspects of assigning 2D pixel values based on 3D voxel column characteristics, according to some embodiments. In FIG. 22, the 3D segmented volume 2200 is depicted. One voxel column 2210 is shown. According to some embodiments, the 2D pixel value for the 2D combined or compounded image can be selected by assigning it to the minimum value found in the voxel column. This option is shown in block 2116 of FIG. 21A. However, it has been found that such an approach in many cases leads to an overly noisy 2D image that is not as useful in facilitating the user's efficient screening. It has been found that better results can often be obtained by assigning the pixel in the 2D image to a value that is not the lowest (darkest) in the voxel column. In block 2114, the voxel column is searched for the darkest contiguous length of a specified extent, such as 2 mm, and the 2D pixel value is assigned to an averaged value of those contiguous voxels. Other lengths besides 2mm can be used depending on the situation. According to some other embodiments, the 2D pixel value is assigned to a value at which 4 percent of the voxels in the column have lower (darker) values. Other amounts besides 4 percent can be used also, depending on the situation. According to some other embodiments, some other method of assigning 2D pixel value is used based on the voxel values. Following a suitable projection method (e.g. 2114, 2116, 2118 or some other method), a 2-D image 2120 is generated.

Figure 23:
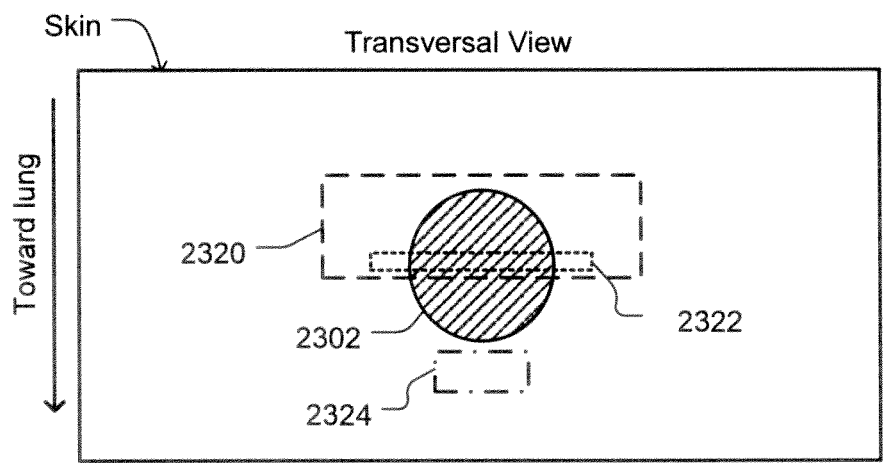
FIGS. 23A and 23B illustrate examples of enhancements of representations of breast abnormalities.
Figure 23:
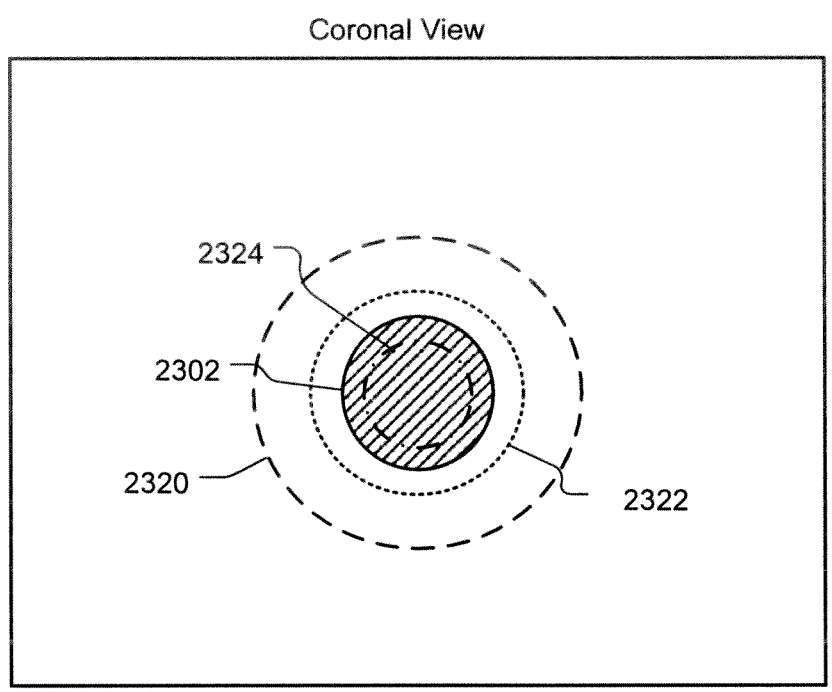

FIGS. 23A and 23B are transverse and coronal views, respectively, illustrating CAD ROI alteration techniques for use in enhanced, whole-breast navigator overview images, according to some embodiments. According to some embodiments, a line enhancement, such as second derivative of voxel filter is applied to voxels inside a sub-volume, shown as Zone 2320. The line enhancement filter is a 2D filter in the coronal plane, i.e. approximately parallel to the chest wall, where the spiculation is most prominent. The size of the sub-volume 2320 in the coronal plane is proportional to, but larger than, the size of the CAD ROI 2302 in the coronal plane. The location of the sub-volume 2320 also includes a region above the CAD-found ROI 2302 as seen in FIG. 23A, since this is also where spiculation is likely to be most prominent. A 2D sub-image is generated by the average voxel value of the line-enhanced sub-volume along the depth direction (skin to lung). The sub-image is then super-imposed directly to the enhanced, whole-breast navigator overview image by a weighted sum of the 2D projection of the navigator overview image and the line enhanced 2D sub-image to enhance the spiculation around the CAD ROI on the enhanced, whole-breast navigator overview.

For likely benign lesions, such as a cyst determined by CAD, the average intensity of several slices immediately behind (or beneath) the CAD ROI is calculated to compose a 2D sub-image. The size of the sub-volume in the coronal plane is proportional to, but smaller than, the 2D size of the CAD-found ROI 2302 in the coronal slice, shown as Zone 2324. The sub-volume 2324 is below (or beneath) the CAD-found ROI 2302, such as shown in FIG. 23A. The pixel value outside the sub-image 2324 is set to zero. The sub-image is then superimposed to the enhanced, whole-breast navigator overview image by weighted sum between the sub-image and the enhanced, whole-breast navigator overview image to indicate the acoustic enhancement of a benign lesion such as a cyst. As result, a benign lesion with acoustic enhancement behind will show in the enhanced, whole-breast navigator overview image as a dark region with a white core inside.

A high-pass or edge enhancement filter is applied to a sub-volume 2322 around a center of a CAD-found ROI 2302 in a coronal slice. The voxel value resulting from the high-pass filter is clipped to zero if the resulting voxel value is less than zero. A 2D sub-image is generated by the average voxel value along the depth direction. The 2D sub-image is then added to the enhanced, whole-breast navigator overview image by a predetermined weight. This creates a rim around the edge of the region for a benign lesion with well-defined border, such as a fibroadenoma.

FIGS. 24A and 24B are transversal and coronal views, respectively, illustrating CAD ROI alteration techniques, according to some embodiments. The techniques described with respect to FIGS. 23A and 23B, supra (line enhancement in zone 2320, high-pass filter in zone 2322, and superimposition from posterior zone 2324) can be applied to a CAD-found ROI simultaneously. In FIGS. 24A and 24B, three CAD-found ROIs 2310, 2320, and 2330 are shown. By applying the alteration techniques such as described with zones or sub-volumes 2320, 2322, and 2324 for each CAD-found ROI, the graphically altered result facilitates distinguishing by a user. ROI 2410 is a typical cancer lesion, and is characterized by a spiculated margin, ill-defined border and no posterior acoustic enhancement. The resulting coronal view 2410 in FIG. 24B, after alteration, is shown as a dark hole with spiculated margin on the enhanced, whole-breast navigator overview image. ROI 2420 is a typical cyst, with a well-defined border, very dark inside the lesion and with a strong posterior acoustic enhancement (light shadow). After alteration, the ROI 2420 in FIG. 24B is shown as a dark hole with white rim around its border and a white core in the center of the dark hole. ROI 2430 is a typical fibroadenoma, with well-defined border, slightly dark inside the lesion and with no posterior acoustic enhancement. After alteration, the ROI 2430 in FIG. 24B is shown as a slightly darker hole with a white rim around its border on the 2D guide image.

Figure 25:
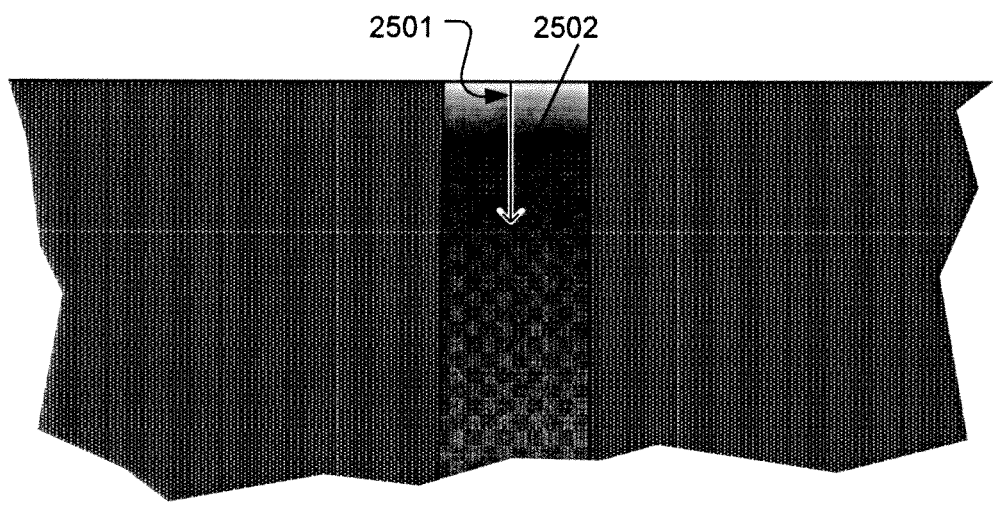
FIG. 25 illustrates an example of treatment of artifacts resulting from an irregularity in acoustic coupling between an ultrasound transducer and a breast being scanned.

FIG. 25 illustrates aspects of a technique for detecting locally poor coupling artifacts, according to some embodiments. In this example, an algorithm is used in a computer module to detect high decreasing gradients (i.e. light-to-dark gradients) in voxel value when moving from the top (skin surface) of the 3-D image volume 2500 downwards, as indicated by arrow 2502. The pixel value profile is calculated along the z-axis (depth). In poor acoustic coupling situations, the pixel value decreases generally linearly and the slope of decrease is much steeper than in the surrounding tissue region. This situation can be classified as an artifact, and can be noted as such or voxel values from its neighborhood can be filled in.

Figure 26:
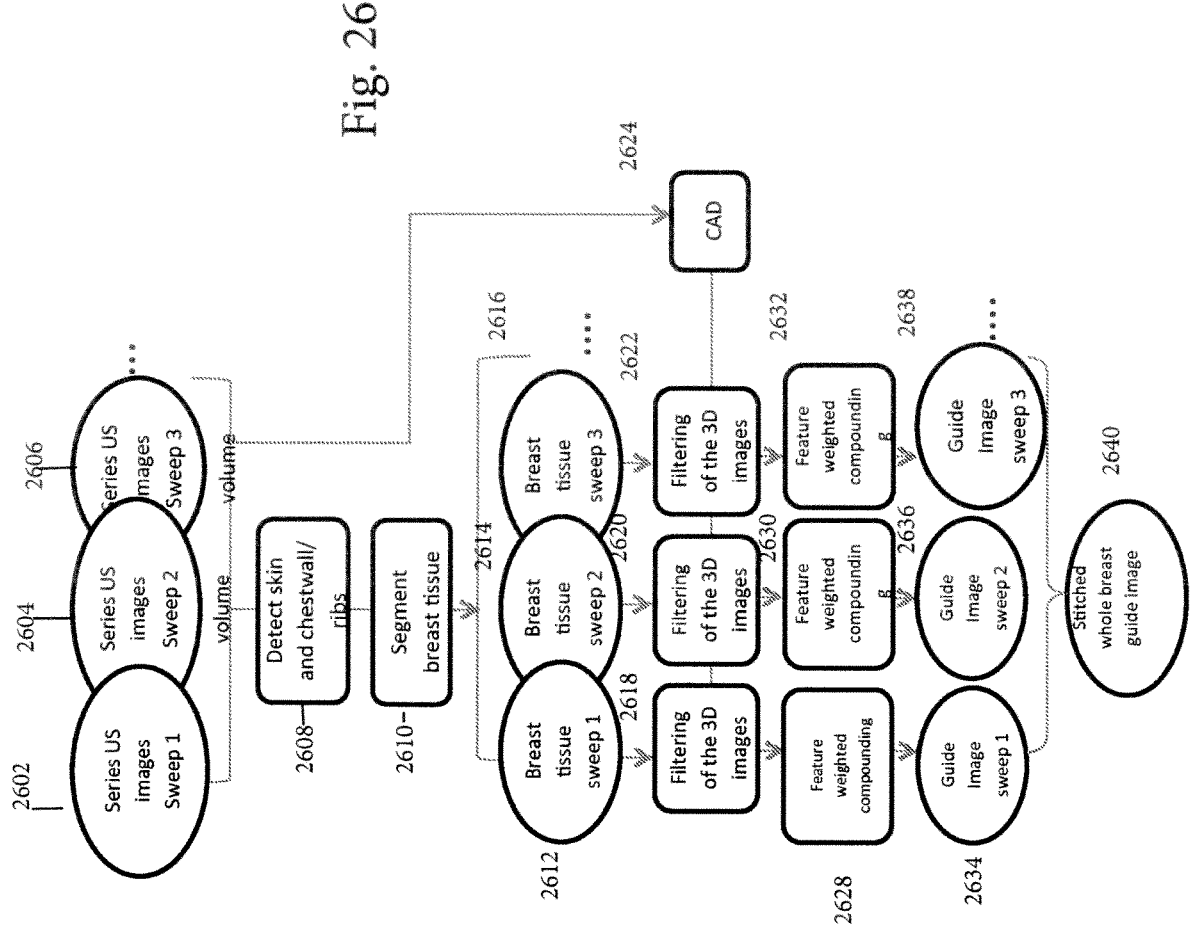
FIG. 26 illustrates an example of computer modules and processes involved in acquiring and acting on ultrasound measurements of a breast and producing and using whole-breast navigator aids and pop-ups.

FIG. 26 illustrates an example of a system and method producing a whole-breast navigator image or aid starting with multiple sweeps of an ultrasound 5 transducer relative to a breast, for example as illustrated in FIG. 16. Computer modules 2602, 2604, and 2606 collect 2D original ultrasound thin-slice images from respective partly overlapping sweeps 1, 2, and 3 of one or more ultrasound transducers over the breast, and represent the hardware involved in obtaining the images as well as computer storage of the resulting original scan measurements or images. A greater or lesser number of sweeps than the three that are illustrated can be used. Each of these modules also constructs a respective 3D structure of the voxel values of tissue scanned with ultrasound in the respective sweep in the case of linear scanning motion of the ultrasound transducer or the respective scanned sector in case of rotary scan with two or more circumferentially spaces transducers or from a rotary scan with a single transducer. A computer module 2608 finds in each of the 3D structures certain volumes that should be segmented out, such as skin and possibly a thin layer underneath, chestwall, and/or ribs, and computer module 2610 segments the desired scanned tissue such as the breast tissue. Computer modules 2612, 2614, and 2616 collect and store the 3D breast tissue voxel measurements for the respective sweeps of the ultrasound transducer that were segmented in module 2610, and supply the voxel measurements to respective filtering computer modules 2618, 2620, and 2622, which apply filtering of the types discussed above. For example, the filtering can include applying CAD algorithms by computer module 2624 to the 3D structures to find likely abnormalities in the breast tissue they represent. Alternatively, or in addition, module 2624 can apply CAD algorithms to the original 2D thin-slice images and/or to the constructed 3D structures in or from modules 2602, 2604, and 2606. The 3D structures with abnormalities found therein are supplied to respective computer modules 2628, 2630, and 2632, which apply thereto feature weighted compounding of the types discussed above to produce enhanced guide images or aids with enhanced representations of found abnormalities for the respective sweeps. These guide images or aids can be 2D projections of the 3D structures for the respective sweeps, and are supplied and stored in respective computer modules 2634, 2336, and 2638. Then, a computer module 2640 stitches or blends the respective guide images or aids into a single whole-breast navigator image or aid that can be displayed as a 2D representation of the 3D structure of the breast and of the found enhanced abnormalities as discussed above, preferably with the pop-up 2D thin-slice image or images for respective abnormalities.

Figure 27:
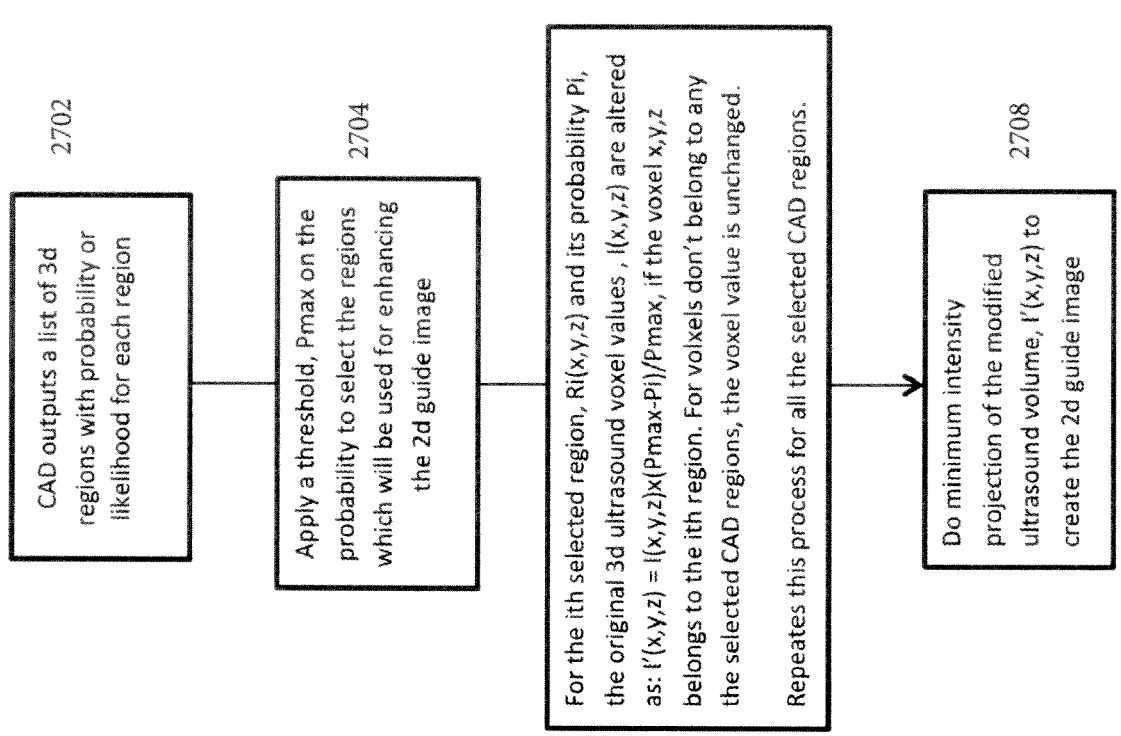
FIG. 27 illustrates and example of computer modules and processes related to applying CAD algorithms to filter ultrasound measurements and results.

FIG. 27 illustrates an example of equipment and method applying CAD algorithms in producing a desired enhanced whole-breast navigator guide. Computer module 2702 applies such algorithms to a 3D structure of voxel values representing breast tissue to find 3D regions "I" that contain likely abnomialities and outputs a list of the found regions and for each a probability Pi that it contains an abnormality. Computer module 2704 applies a threshold Pmax to the probabilities Pi for respective found regions "i" thereby selecting regions that would be used to enhance abnormality representations in the ultimate whole-breast enhanced navigator aid image. Computer module 2706 then uses the results to alter voxel values related to the selected regions. For example, for the i-th selected 3D region Ri(x,y,z) and its probability Pi, the previously found voxel values I(x,y,z) are altered into values I'(x,y,z)=I(x,y,z)×(Pmax−Pi)/Pmax, if the voxel (x,y,z) in in that i-th region. For voxels that are outside a region containing suspected abnormality, the voxel value is unchanged. The process is repeated for each voxel in each found region of a suspected abnormality. Computer module 2708 then produces for display a 2D representation of the resulting altered 3D breast structure, for example by a minimum intensity projection of the 3D structure that includes the modified voxel values I'(x,y,z).

The several examples of whole-breast navigator aids can be used for temporal comparison with similar aids obtained for the same breast in prior studies to find changes in abnormality parameters with time or to confirm that there have been no changes. For example, the size of a found abnormality can be compared based on two studies of the same breast taken at different times, or the probabilities Pi can be compared.

Figure 28:
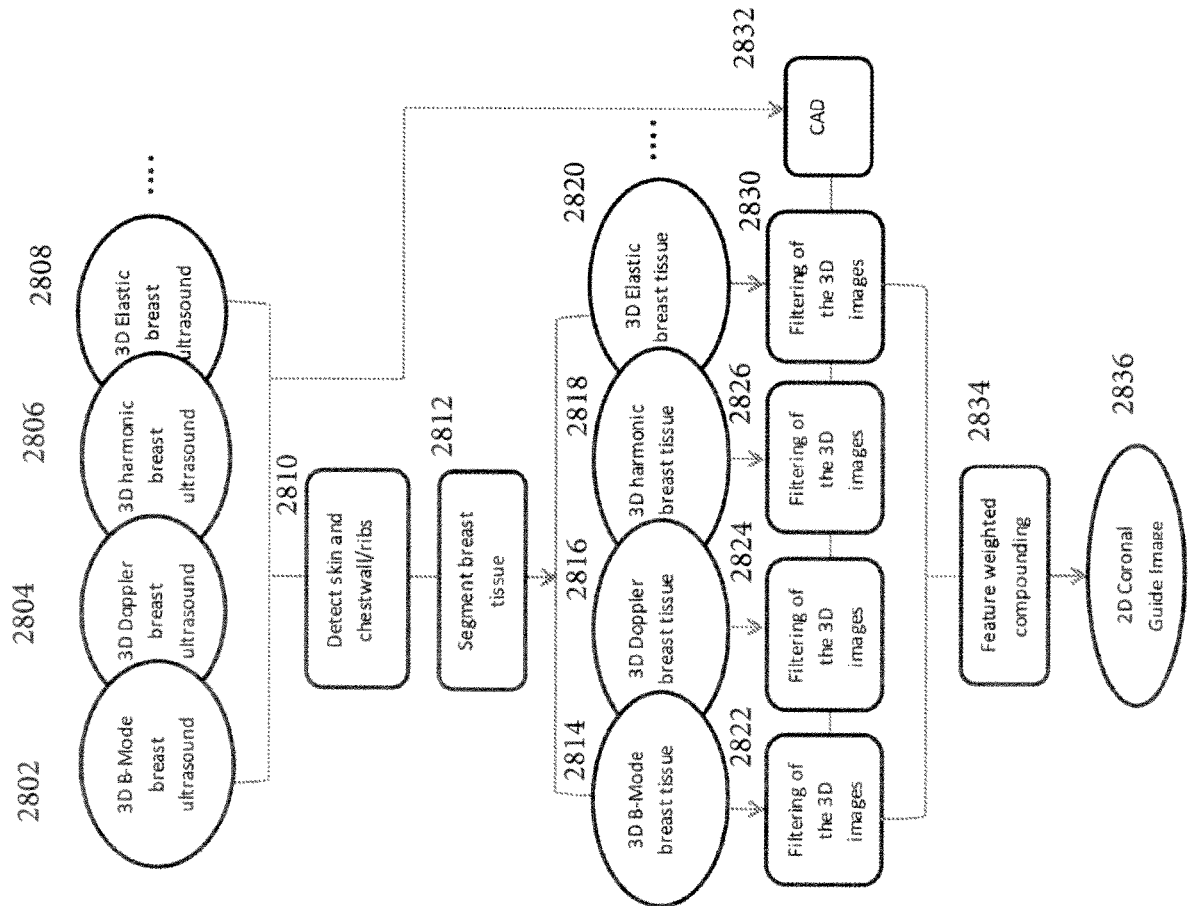
FIG. 28 illustrates an example of computer modules and processes related to using multi-mode ultrasound measurements to produce an enhanced whole-breast navigator aid and related pop-ups.

FIG. 28 illustrates an example of equipment and method that involve taking and using multi-mode sonographic breast measurements. In addition to the regular B-mode, breast ultrasound can be operated at other modes to further characterize breast tissue. For example, Doppler ultrasound can evaluate angiogenesis, while elastography can evaluate the stiffness of a region of interest. An example of such use of several modes is to create a combined whole-breast enhanced navigator guide or aid. To this end, modules 2802, 2804, 2806, and 2808 scan a breast with ultrasound transducers in the indicated respective modes, and from the sonographic responses produce respective 3D structures of the scanned tissue. Only two modes can be used, or more than the four indicated modes. These modules produce respective 3D structures of the scanned tissue such as a 3D set of voxel values. Each voxel is a representation of the ultrasound response at a given mode from the corresponding location in the patient's anatomy. Geometrically, the 3D structure can have one rectangular face, generally parallel to the chestwall, which face closely corresponds to the surface of the breast against which the ultrasound transducer was compressed during scanning. The typical scanned tissue includes breast tissue as well as some muscle, ribs, and possibly lung tissue, and also contact artifacts and other structures that are incidental to the scan. Using all measurement from all desired scans, computer module 2810 finds and segments out selected non-breast structures, preferably those external to the breast such as the ribs, chest muscle, and lung regions. Scan artifacts caused by poor acoustic coupling and other problems and certain skin or thin regions near or next to the transducer can also be segmented out in the same module or identified for correction or corrected. After the removal of influences of undesired structures by segmentation, the scanned 3D breast tissue (including fat, glandular tissue, and any abnormalities internal to the breast) as represented in a 3D structure of voxels in each mode, is collected and stored in respective computer modules 2814, 2816, 2818, and 2820, and the respective 3D structures are filtered by a group of filter modules 2822, 2824, 2826, and 2830, which are designed to suppress noise, remaining artifacts, and to enhance abnormalities or lesions for any given mode as discussed above. As an example, the filters for the B-Mode image can be the gradient conversion filter and line conversion filter. The gradient conversion filter is designed to enhance the dark rounded shapes, and the line conversion filter is designed to enhance lines radiating from a center which resembles a speculation or architecture distortion. The gradient conversion filter can also be applied on the elastography volume to enhance the concentrated stiff voxels. The final step is to apply feature weighted compounding. Computer module 2832 can apply CAD algorithms in the course of such filtering, and/or to the respective measurements from modules 2802,02804, 2806, and 2808.

Computer module 2834 applies weighted compounding to the filtered 3D structures. The weights, w(x,y,z) for compounding can be produced by combining the outputs of the filters of all modes, as represented by the expression $$w(x, y, z) = \sum_{m}^{M} \sum_{i}^{N_m} k_{mi} f_{mi}(x, y, z)$$

where M is the total number of modes while Nm is the total number of filters of mode m, fmi (x, y, z) is the output of ith filter of mode m, and kmi is a constant scaling factor for ith filter of mode m. The weight is also normalized from 0 to 1 as the probability of a voxel overlap with a cancer lesion.

Figure 29:
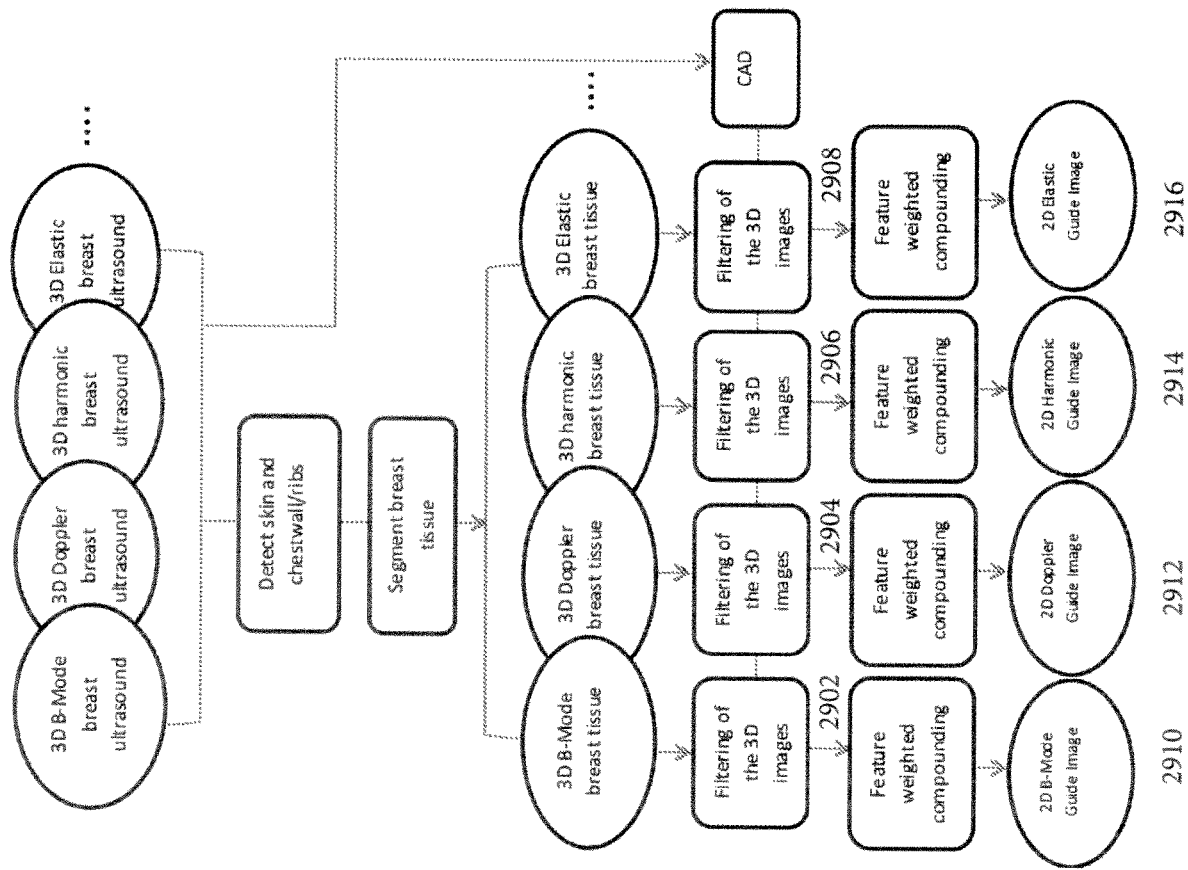
FIG. 29 illustrates another example involving the use of multi-mode ultrasound measurements.

FIG. 29 illustrates equipment and methods that are otherwise the same or similar to FIG. 28 except that a separate whole-breast navigator guide or aid is produced for each respective ultrasound modality. The modules that are the same as in FIG. 28 bear the same labels and are not numbered. The modules that are different are the multiple feature weighted compounding modules that replace the single module 2834 in FIG. 28, and the plural guide image modules that replace module 2836 of FIG. 28.

An example of equipment and method producing and using a whole-breast navigator aid and related pop-ups involves segregating the ultrasound measurements by frequency content into low- and high-frequency components and producing a 3D structure of the scanned tissue that is a weighted combination of the low-pass (background) and high-pass (signal) components. This can be accomplished by subjecting the 3D structure produced as discussed above to computer-processing through algorithms producing a background 3D structure through techniques such as non-linear smoothing, in which case the background component is not strictly "low-pass" in the traditional sense, but emphasizes low frequency image content while suppressing high-frequency content. Concurrently, computer-processing can subject the starting 3D structure to a high-pass filtering to emphasize the high-frequency (signal) content while suppressing the low-frequency content. A simple summation of these derived background and signal components of the 3D structure of breast voxel values should reproduce the original 3D structure faithfully. In order to enhance the type of navigator aid discussed above, the summation that a computer module carries out can be simple summation outside of 3D regions of interest (ROIs) that CAD or other filtering has identified as discussed above but a weighted summation for the ROIs, with the signal component emphasized in the neighborhood of the found ROIs. This variable-weighted 3D structure is then be subjected to computer processing to carry out a projection such as a minimum intensity projection (MinIP) in which subtle details such as spiculations are enhanced and made more evident than in a MinI P on an unprocessed original volume. The intensity contrast of the lesion itself is enhanced as well, possibly obviating the need to apply an explicit intensity bias, which may reduce the impact of CAD false positives on the navigator guide image or aid.

According to some embodiments, bookmarks are added to abnormalities after the user has had a chance to evaluate them. The bookmarks can be color, possibly indicative of the importance that the user ascribes to an abnormality, a BIRAD score, a simple mark such as a circle around an examined abnormality, and/or some other mark that can serve as a reminder of the user's work with the examined images.

Processing according to the embodiments described above can be carried out in the ultrasound engine and/or workstation equipment used in the current commercial automated breast ultrasound systems, when running programmed algorithms according to software that a skilled person can write without undue experimentation based on this patent specification and knowledge of the processing in the commercial systems. Some of the functions can be implemented using firmware or hardware instead of or in addition to software According to some embodiments, interactive user interface methods and systems are described that can shorten the time to view and assess important breast ultrasound images within a time limit of approximately 3 minutes and with low oversight.

According to some embodiments, a novel CAD-driven navigator overview image display method and system are disclosed. The navigator overview image is configured to assist the readers to reduce their reading/interpretation time and at the same time to provide comfort and confidence such that oversights would be reduced.

According to some embodiments, the display method and system show to the readers the abnormalities in a navigator overview image derived from 3D volumetric scans, where the abnormalities were image processed, with little or no traditional CAD involved, by displaying at each pixel location a combined, e.g., a low average, value selected from a set of voxels in a voxel column that can be oriented in the chestward direction. According to some other embodiments, the navigator overview image is more CAD driven, where CAD is employed to detect and enhance the displayed abnormalities. According to yet other embodiments, CAD is employed to detect both malignant-looking abnormalities as well as benign-looking abnormalities. The navigator overview image displays additional features, showing both malignant and benign characteristics in a way to classify these abnormalities, to enable the readers to place higher priority on viewing the more suspicious abnormalities. Thus, this would further reduce the reading/interpretation time. CAD is important in detecting and thus reducing obvious oversights. CAD marks or CAD probability figures can be displayed anytime (before, during or after readers looked the navigator overview image) at the readers preference or as preset for the equipment.

According to some embodiments, a method and system for processing and displaying breast ultrasound information are provided, wherein a feature weighted volumetric navigator overview image is generated from the 3D ultrasound data volume to represent the 3D dataset with the goal of emphasizing abnormalities found within the breast while excluding some or all non-breast tissue or structures, particularly those external to the breast such as ribs and chest wall, and optionally skin and immediately adjacent tissue, in accordance with the method and system described herein.

According to some embodiments, the navigator overview image is displayed in addition to and together with a display of images available in current commercial automated 3D breast ultrasound systems employing chestward compression scans, where a 2D original axial scan image, and a 2D orthogonal (constructed to be orthogonal to the axial scan) image are displayed with 2D coronal thick-slice images. By clicking any exhibited abnormality in the navigator overview image, with pre-calculated xyz coordinates, the corresponding abnormality can show up in the 2D coronal thick-slice image, as well as at the corresponding locations in the 2D original axial scan image and the orthogonal sagittal image.

According to some embodiments, the navigator overview image is displayed together with just the 2D original axial scan image for the quickest review and a snippet of one or more 2D images of coronal thick-slices. It is sometimes useful to show the coronal thick-slice image, because readers may like to confirm their assessment by examining the presence of spiculations of a mass nodule that only show, or show better, in composite coronal thick-slices. The quick review of the 2D axial scan images can be done in the manner described above.

According to some embodiments, the navigator overview image is displayed in inverted polarity. That is, in a regular display, the abnormalities are dark colored on relatively light breast tissue background, and in the inverted polarity, the abnormalities are light colored on a relatively dark breast tissue background. Some readers may find it more useful to read the inverted polarity guides, which resemble mammograms (also with lighter colored abnormalities such as calcifications on a darker background).

According to some embodiments, the navigator overview image is generated through a process of segmenting away non-breast structure and using a filter to enhance the remaining volumetric breast tissue to make the abnormalities more visible and more prominent.

According to some embodiments, the filter includes a computer aided detection (CAD) algorithm that detects and ranks the lesions by likelihood. This is particularly useful for very small abnormalities or lesions that show significant likelihood of being malignant by CAD, and yet the above described filter may not be enough to make these small abnormalities as visible or prominent in the navigator overview image.

According to some embodiments, additional information is shown with an abnormality such as its size, volume, relative probability, likelihood of being malignant, etc.

According to some embodiments, the navigator overview image is displayed on a separate monitor situated for convenient viewing, e.g., adjacent to the display monitor of a commercial automated 3D breast ultrasound system while in other embodiments all images are on the same screen, which also may show other information.

According to some embodiments, two or more navigator overview images are displayed, typically concurrently, each for a respective breast of the patient or for a respective scan of a breast with an ultrasound transducer, while in other embodiments different images can alternate or be superimposed, possibly with different degrees of transparency.

According to some embodiments, the navigator overview image is displayed on a separate sheet of paper to be viewed with the display monitor of a commercial automated 3D breast ultrasound system.

The computer modules or steps described in this patent specification can be implemented in special purpose computer equipment, or in individual programmed computer modules, or in a lesser number of computer modules or even a single computer system programmed in accordance with the disclosure herein to carry out the required processes.

While several embodiments are described, it should be understood that the new subject matter described in this patent specification is not limited to any one embodiment or combination of embodiments described herein, but instead encompasses numerous alternatives, modifications, and equivalents. In addition, while numerous specific details are set forth in the following description in order to provide a thorough understanding, some embodiments can be practiced without some or all of these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features or other described embodiments. Further, like reference numbers and designations in the various drawings indicate like elements.

Various modifications may be made without departing from the spirit and scope of the new methods and systems described in this patent specification. Accordingly, the scope of this patent specification is not limited to the above-described embodiments, but instead is defined by the claims of a patent to issue thereon in light of their full scope of equivalents.

What is claimed is:

1. A system for ultrasound examination of a patient's breast, comprising:
    an ultrasound transducer device compressing chestwardly a breast of a recumbent patient and scanning the breast with one or more ultrasound transducers in a rotary motion of an essentially planar scanning template to thereby produce original two-dimensional (2D) ultrasound images of the breast;
    a processor configured to receive the original images and to (s) apply computer processing algorithms thereto to produce a three-dimensional (3D) representation of ultrasound responses of respective volume elements (voxels) of the scanned breast, (b) to find suspected abnormalities in breast tissue that is inward of regions of skin, ribs, and pectoral muscle, including by taking into account shape properties of potential abnormalities, and (c) to produce a whole breast navigator structure depicting the entire breast tissue that is inward of said regions;
    wherein said whole breast navigator structure comprises a selected 2D projection of breast tissue that is inward of said regions and of the suspected abnormalities found therein; and a computer display configured to:
  produce and display a depiction of the whole-breast navigator structure with said suspected abnormalities therein; and
  respond automatically to drawing attention to a suspected abnormality in the whole breast navigator structure by producing and concurrently displaying a pop-up depiction of the abnormality as it appears in an image of the breast tissue.

2. The system of claim 1 in which the processor is further configured to highlight selected representations of found tissue abnormalities by making the displayed locations of likely malignant abnormalities darker or lighter in the whole breast navigator structure than if not highlighted.

3. The system of claim 1 in which the processor is further configured to boost conspicuity in the displayed whole breast navigator structure of representations of locations of abnormalities that are likely spiculations.

4. The system of claim 1 in which the processor is further configured to boost conspicuity of representations in the displayed whole breast navigator structure of abnormalities that are a likely cyst and enhance the representation of an image of a cyst by placing a spot therein that differs from a remainder of the cyst image.

5. The system of claim 1 in which the processor is further configured to detect and remove influences of ultrasound responses resulting from poor ultrasound transducer-to-breast coupling.

6. The system of claim 1 in which the processor is further configured to produce the whole breast navigator structure through a process comprising assigning to a pixel in a projection of the whole breast navigator structure a value related to the darkest voxel value in a positionally related column of voxel values.

7. The system of claim 1 in which the processor is further configured to produce the whole breast navigator structure through a process comprising assigning to a pixel in a projection of the whole breast navigator structure a value related to voxel values along a stretch of 1-3 mm containing the darkest voxel values of a positionally related column of voxel values.

8. The system of claim 1 in which the processor is further configured to produce the whole breast navigator structure through a process comprising assigning to a pixel in a projection of the whole breast navigator structure a value related to only some of the voxel values of a positionally related column of voxel values.

9. The system of claim 1 in which the ultrasound transducer compresses and scans the breast of a recumbent patient who is supine.

10. A system for automated ultrasound examination of one or both of a patient's breasts, comprising:
  a source of a sonographic response acquired by chestwardly compressing a breast of a recumbent patient and scanning the compressed breast tissue with ultrasound emitted and received by an ultrasound transducer electrically and/or mechanically driven for a rotary scanning motion relative to the breast;
  a programmed computer processor configured to apply computer image processing algorithms to the sonographic response thereby producing a three-dimensional(3D) structure representing ultrasound responses for volume elements (voxels) of the scanned breast;
  said processor being configured to apply computer processing algorithms to (i) segment out influences of non-breast tissue, (ii) find suspected tissue abnormalities in the 3D structure remaining after said segmenting, including by accounting for sonographic responses related to patches of plural voxels inand/or out of a suspected abnormality;
  said processor thereby producing a single navigator overview image per breast, and being configured to apply filtering algorithms enhancing representations of suspected abnormalities to thereby produce conspicuity enhancements of one or more of the found tissue abnormalities in each of the navigator overview images; and
  a computerized display configured to display each of the breast navigator overview images in association with one or more other images that are automatically selected and/or generated from the sonographic responses and include one or more representations of a selected abnormality found in the navigator overview image.

11. The system of claim 10 in which the processor is configured to form and display one or more reduced-size images of the breast navigator overview images, and the display is configured to concurrently display at least one image of a breast slice that conforms to a chestwardly oriented plane and contains an abnormality present in a selected one of the breast navigator overview images.

12. The system of claim 10 in which the recumbent patient is supine.

13. A system for automated ultrasound examination of a patient's breasts, comprising:
  a source of sonographic responses acquired by compressing the patient's breasts chestwardly while the patient is recumbent and scanning the compressed breast tissue with one or more sonographic transducers electrically or mechanically driven to scan the breasts in a rotary motion of a scanning template;
  a programmed computer processor configured to apply computer image processing algorithms to the sonographic responses thereby producing a plurality of whole-breast navigator overview images each representing a three-dimensional breast volume with abnormalities therein found through filtering with said algorithms;
  said processor being configured to produce each of said plurality of whole-breast navigator overview images by (i) producing from said sonographic responses a three-dimensional (3D) structure representing volume elements (voxels) of scanned tissue, (ii) segmenting out influences of non-breast tissue in said sonographic responses and finding tissue abnormalities in remaining whole-breast 3D structure, including by comparing sonographic responses for portions of the breast with ultrasound responses for other portions of the breast and accounting for shape properties of potential abnormalities, and (iii) producing conspicuity enhancements of at least some of the found tissue abnormalities;
  a computerized display configured to display two or more of the plurality of whole-breast navigator overview images to a user, the processor being further being configured to respond to a selection by a user of region of interest (ROI) in a whole breast navigator overview image to cause a display of one or more other images generated from the sonographic response that are associated with the user-selected ROI.

14. The system of claim 13 wherein the selection of the ROI by the user is made by dwelling a pointing device on the ROI on the computer display.

15. The system of claim 13 wherein one or more other images include at least a portion of an original two-dimensional thin-slice scan image, wherein said thick-slice image represents a slice of the patient's breast that is thicker than a slice of the breast represented by said thin-slice image.

16. The system of claim 13 wherein the processor is further configured to respond to a user input to successively display additional images generated from the sonographic response in the vicinity of the ROI.

17. The system of claim 13 in which the ultrasound transducer compresses and scans the breast of a supine patient.

18. A method of ultrasound examination of a patient's breast, comprising:

compressing a patient's breast chestwardly while the patient is recumbent;

scanning the compressed breast with an ultrasound transducer through a gel-impregnated membrane in a rotary scanning motion relative to the breast while sending ultrasound energy into the breast and receiving ultrasound energy from scanned tissue, thereby producing ultrasound responses for breast slices that conform to planes extending in chestward directions;

applying computer processing to the ultrasound responses to thereby produce a three-dimensional (3D) structure representing sonographic response characteristics of volume elements (voxels) of scanned tissue;

applying computer processing algorithms to at least one of (i) the ultrasound responses and (ii) the 3D structure to thereby segment out influences of selected scanned tissue and to find tissue abnormalities in the remaining 3D structure;

applying further computer processing algorithms to the remaining 3D structure to thereby produce conspicuity enhancements of at least some of the found tissue abnormalities;

applying further computer processing to the 3D structure to thereby produce two-dimensional (2D) breast navigator image depicting the scanned breast and abnormalities therein that have been enhanced;

displaying a depiction of the 2D breast navigator image with abnormalities therein; and responding to an input regarding an abnormality in the 2D breast navigator image or the 3D structure by producing and concurrently displaying a pop-up depiction of the abnormality as it appears in one of said breast slices that conform to planes extending in chestward directions.

19. The method of claim 18 in which the producing of conspicuity enhancements comprises making likely malignant abnormalities darker or lighter in the 2D navigator image than likely non-malignant abnormalities.

20. The method of claim 18 in which the compressing step comprises compressing the breast of a recumbent patient who is supine.

* * * * *